US011112404B2

(12) United States Patent
Akama et al.

(10) Patent No.: US 11,112,404 B2
(45) Date of Patent: Sep. 7, 2021

(54) METHOD FOR OBTAINING INFORMATION OF TEST SUBSTANCE

(71) Applicant: SYSMEX CORPORATION, Kobe (JP)

(72) Inventors: Kenji Akama, Kobe (JP); Toshihiro Watanabe, Kobe (JP); Masaya Okada, Kobe (JP); Kazuto Yamashita, Kobe (JP); Akshay Ganguly, Kobe (JP); Shigeki Iwanaga, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 598 days.

(21) Appl. No.: 15/951,375

(22) Filed: Apr. 12, 2018

(65) Prior Publication Data

US 2018/0299437 A1 Oct. 18, 2018

(30) Foreign Application Priority Data

Apr. 13, 2017 (JP) .............................. JP2017-079793

(51) Int. Cl.
| | |
|---|---|
| *G01N 33/543* | (2006.01) |
| *C07K 16/18* | (2006.01) |
| *G01N 33/533* | (2006.01) |
| *G01N 33/68* | (2006.01) |
| *G01N 33/58* | (2006.01) |

(52) U.S. Cl.
CPC ....... *G01N 33/54326* (2013.01); *C07K 16/18* (2013.01); *G01N 33/533* (2013.01); *G01N 33/5436* (2013.01); *G01N 33/54353* (2013.01); *G01N 33/54366* (2013.01); *G01N 33/582* (2013.01); *G01N 33/6896* (2013.01); *C07K 2317/70* (2013.01); *C07K 2317/92* (2013.01); *C07K 2317/94* (2013.01); *G01N 2333/4709* (2013.01)

(58) Field of Classification Search
CPC ....... G01N 33/54326; G01N 33/54353; G01N 33/5436; G01N 33/54366; G01N 33/533; G01N 33/6896; G01N 33/582; G01N 2333/4709; C07K 16/18; C07K 2317/92; C07K 2317/70; C07K 2317/94
USPC ........................................................ 436/528
See application file for complete search history.

(56) References Cited

U.S. PATENT DOCUMENTS

| | | | |
|---|---|---|---|
| 8,222,047 B2 | 7/2012 | Duffy et al. | |
| 2006/0115907 A1 | 6/2006 | Klause et al. | |
| 2009/0087869 A1 | 4/2009 | Fujimoto et al. | |
| 2010/0075407 A1* | 3/2010 | Duffy ............... | G01N 33/54313 435/287.2 |
| 2010/0261292 A1 | 10/2010 | Glezer et al. | |
| 2015/0024512 A1 | 1/2015 | Willbold et al. | |
| 2016/0161481 A1 | 6/2016 | Willbold et al. | |
| 2018/0024128 A1 | 1/2018 | Sato et al. | |

FOREIGN PATENT DOCUMENTS

| | | |
|---|---|---|
| CA | 2858125 A1 | 6/2013 |
| CN | 1766621 A | 5/2006 |
| CN | 100489529 C | 5/2009 |
| CN | 101435825 A | 5/2009 |
| CN | 101609090 A | 12/2009 |
| CN | 104080807 A | 10/2014 |
| JP | 2000-105236 A | 4/2000 |
| JP | 2003-107089 A | 4/2003 |
| JP | 2016-524151 A | 8/2016 |
| WO | 2016/159319 A1 | 10/2016 |

OTHER PUBLICATIONS

Zhang, "Super-Resolution Microscopy of Cerebrospinal Fluid Biomarkers as a Tool for Alzheimer's Disease Diagnostics", Journal of Alzheimer's Disease, 46 (2015) 1007-1020.*
Sujin Ahn et al., "Ultrasensitive Detection of [alpha]—Fetoprotein by Total Internal Reflection Scattering-Based Super-Resolution Microscopy for Superlocalization of Nano-Immunoplasmonics", Analytical Chemistry, vol. 88, No. 22, dated Nov. 4, 2016, pp. 1-7.
Chinese Office Action dated Nov. 30, 2020 in a counterpart Chinese patent application No. 201810329376.5.
Communication pursuant to Article 94(3) EPC dated Mar. 19, 2020 in a counterpart European patent application No. 18166773.4.
Zhang, W. et al., "Super-Resolution Microscopy of Cerebrospinal Fluid Biomarkers as a Tool for Alzheimer's Disease Diagnostics", *Journal of Alzheimer's Disease*, vol. 46, 2015, pp. 1007-1020.W.
Wang-Dietrich, L. et al., "The Amyloid-β Oligomer Count in Cerebrospinal Fluid is a Biomarker for Alzheimer's Disease", *Journal of Alzheimer's Disease*, vol. 34, 2013, pp. 985-994.
Communication pursuant to Article 94(3) EPC dated Oct. 6, 2020 in a counterpart European patent application No. 18166773.4.
Susanne Aileen Funke: "Detection of Soluble Amyloid-β Oligomers and Insoluble High-Molecular-Weight Particles in CSF: Development of Methods with Potential for Diagnosis and Therapy Monitoring of Alzheimer's Disease, International Journal of Alzheimer's Disease", vol. 2011, Article ID 151645, 2011, pp. 1-8.
Harry Levine III: "Alzheimer's β-peptide oligomer formation at physiologic concentrations", Elsevier Inc., Analytical Biochemistry, vol. 335, 2004, pp. 81-90.
Japanese Office Action dated Jan. 5, 2021 in a counterpart Japanese patent application No. 2017-079793.
Communication pursuant to Article 94(3) EPC dated Oct. 11, 2019 in a counterpart European patent application No. 18166773.4.

* cited by examiner

*Primary Examiner* — Ann Y Lam
(74) *Attorney, Agent, or Firm* — Crowell & Moring LLP

(57) ABSTRACT

Disclosed is a method for obtaining information of a test substance, the method including: forming a complex by causing a capture substance to bind to a test substance in a specimen; selectively collecting at least the complex from the specimen; immobilizing the complex collected from the specimen, onto a base plate; and obtaining information regarding a structure of the test substance from the complex immobilized on the base plate.

20 Claims, 19 Drawing Sheets

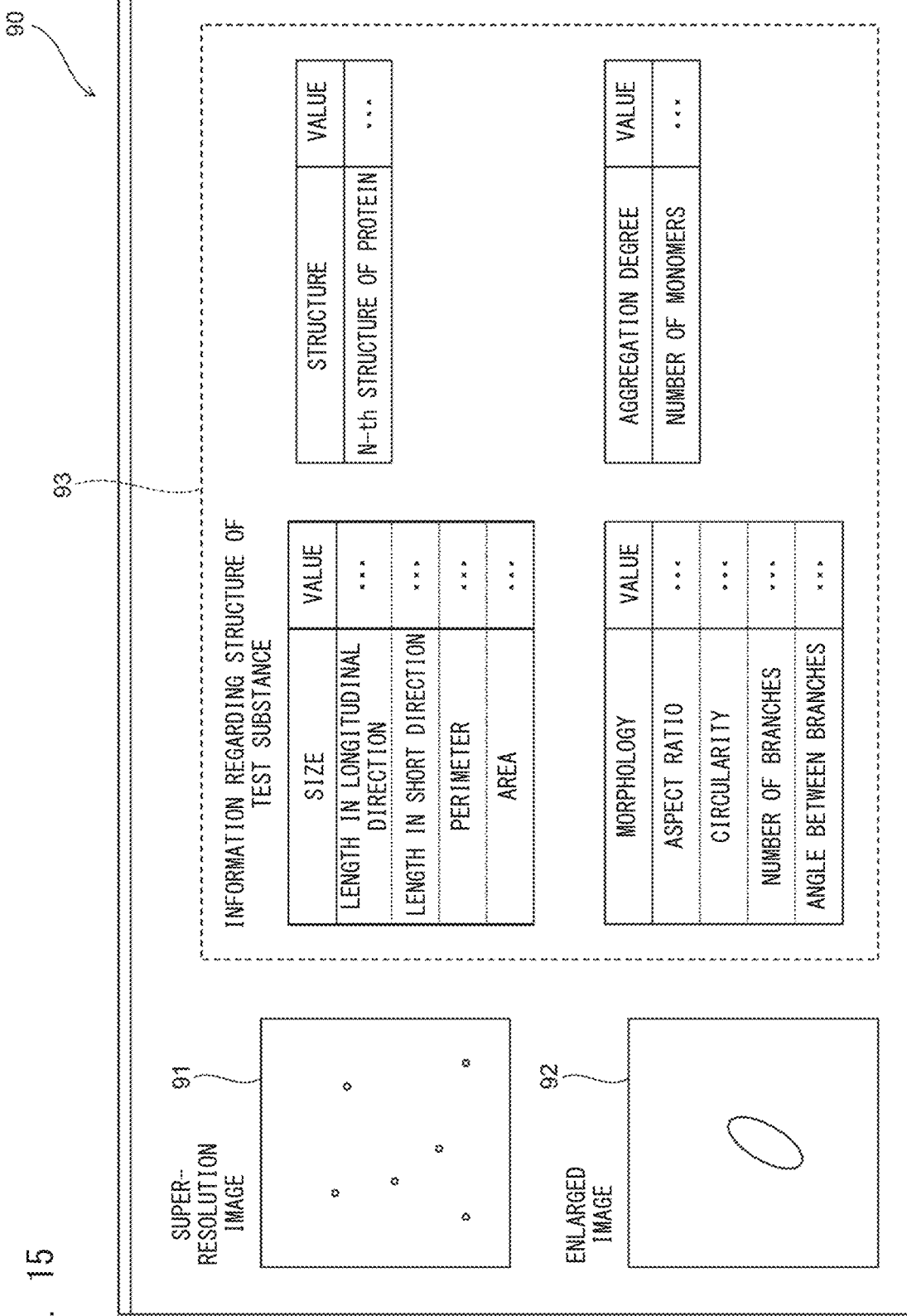

FIG. 16A  EMBODIMENT 1
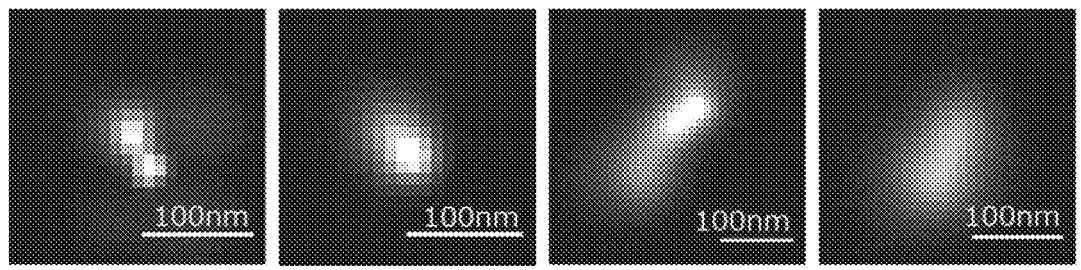
FIG. 16B  EMBODIMENT 1
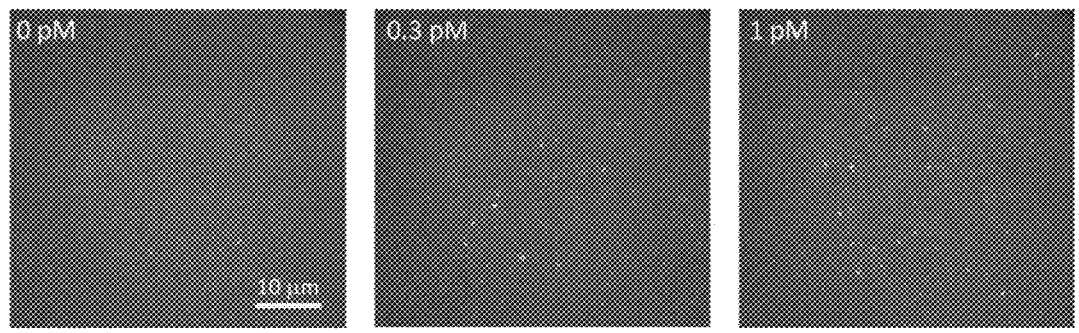
FIG. 16C  EMBODIMENT 1
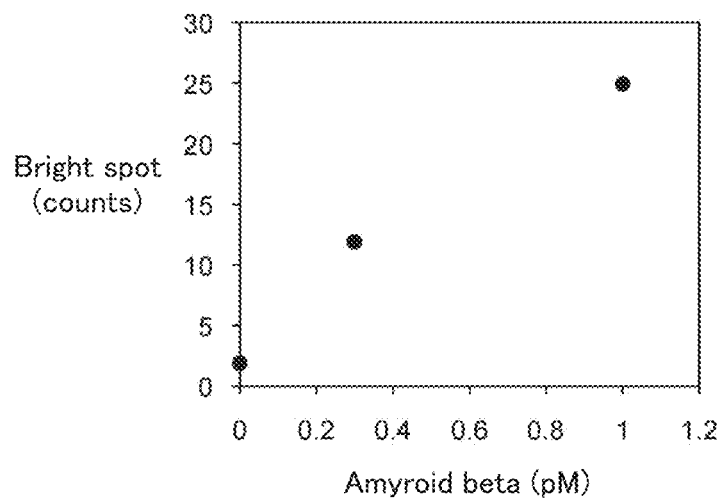

FIG. 17A COMPARATIVE EXAMPLE
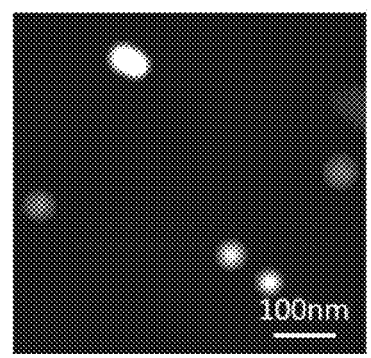
FIG. 17B COMPARATIVE EXAMPLE
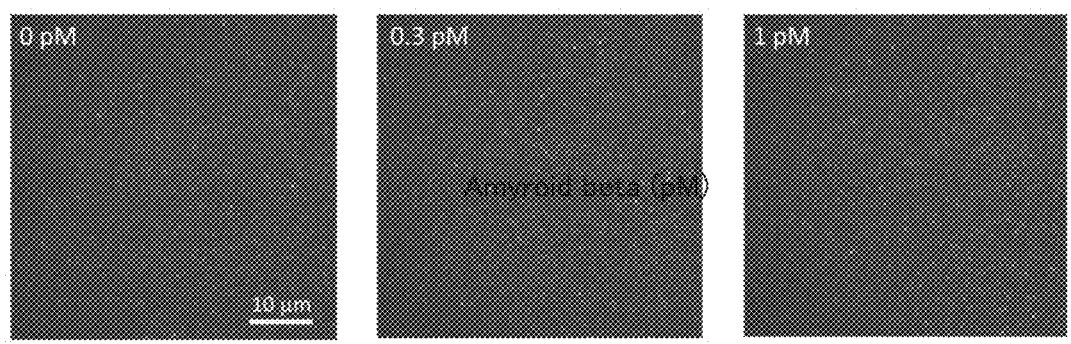
FIG. 17C COMPARATIVE EXAMPLE
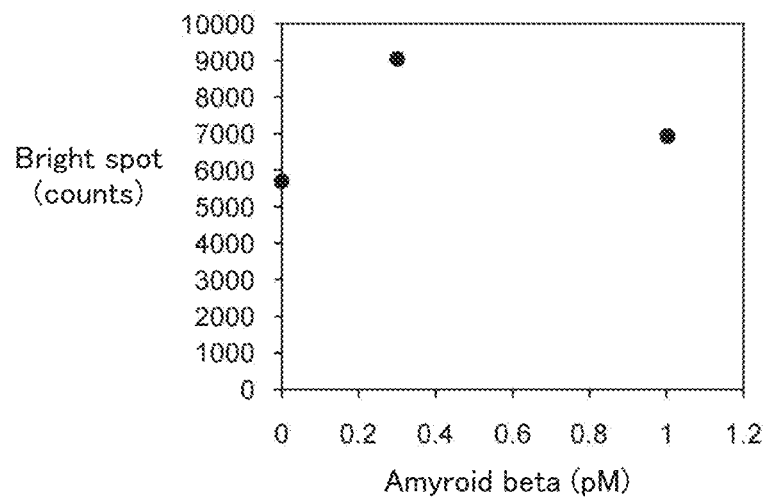

METHOD FOR OBTAINING INFORMATION OF TEST SUBSTANCE

CROSS REFERENCE TO RELATED APPLICATIONS

This application claims priority from prior Japanese Patent Application No. 2017-079793, filed on Apr. 13, 2017, entitled "METHOD FOR OBTAINING INFORMATION OF TEST SUBSTANCE", the entire content of which is incorporated herein by reference.

FIELD OF THE INVENTION

The present invention relates to an information obtaining method for obtaining information from a test substance.

BACKGROUND

Obtaining information regarding the structure of a test substance in a sample is useful in pathological diagnosis and determination of an administration policy. For example, in the case of Alzheimer's disease, the structure (size, length, aspect ratio, etc.) of the test substance such as amyloid $\beta$ changes in accordance with progression of the disease. Thus, if information regarding the structure is obtained from the test substance, the disease condition can be properly understood. Examples of diseases caused by denaturation of protein include Huntington's disease, Parkinson's disease, prion, and ALS (amyotrophic lateral sclerosis), in addition to Alzheimer's disease.

"Super-resolution Microscopy of Cerebrospinal Fluid Biomarkers as a Tool for Alzheimer's Disease Diagnostics" by William I. Zhang and five other authors, Journal of Alzheimer's Disease 46, Mar. 27, 2015, pp. 1007-1020 (hereinafter, referred to as "Non-Patent Literature 1") describes the following: as shown in FIG. 19A, CSF (cerebrospinal fluid) is supplied on a glass base plate 200 to cause an amyloid $\beta$ 211 as a test substance to be physically adsorbed; then, as shown in FIG. 19B, the labeled antibody 230 is caused to bind to the amyloid $\beta$ 211 through a primary antibody 220; and an image is detected by a super-resolution microscope.

According to the technique of Non-Patent Literature 1, as shown in FIG. 19A, not only the amyloid $\beta$ 211 but also an impurity 212 attach to the glass base plate 200. In some cases, the primary antibody 220 and the labeled antibody 230 nonspecifically bind also to the impurity 212 attached to the glass base plate 200. In such a case, as shown in FIG. 19B, the impurity 212 is labeled with the labeled antibody 230. Further, in some cases, the labeled antibody 230 nonspecifically binds to the glass base plate 200. In such a case, as shown in FIG. 19B, a portion of the glass base plate 200 is labeled with the labeled antibody 230. Thus, when not only the amyloid $\beta$ 211 but also the impurity 212, the glass base plate 200, and the like are labeled with the labeled antibody 230, information regarding the structure of the amyloid $\beta$ 211 as a test substance cannot be accurately obtained.

SUMMARY OF THE INVENTION

The scope of the present invention is defined solely by the appended claims, and is not affected to any degree by the statements within this summary.

A first mode of the present invention relates to a method for obtaining information of a test substance. A method for obtaining information of a test substance according to the present mode includes: forming (S11 to S13, S21, S22) a complex (60, 61) by causing a capture substance (30, 40, 50) to bind to a test substance (11) in a specimen (10); selectively collecting (S14, S15, S23, S24) at least the complex (60, 61) from the specimen (10); immobilizing (S16, S26) the complex (60, 61) collected from the specimen (10), onto a base plate (80); and obtaining (S17, S27) information regarding a structure of the test substance (11) from the complex (60) immobilized on the base plate (80).

The specimen is a liquid taken from a living body, and is CSF (cerebrospinal fluid), blood, plasma, interstitial fluid, or urine, for example. The test substance is a cell, a polypeptide, a protein, a nucleic acid, an exosome, a carbohydrate chain, or the like, and in the method for obtaining the information of the test substance according to the present mode, a multimer is appropriate. The test substance is an amyloid $\beta$ oligomer which is made up of polymerized amyloid $\beta$ monomers, a tau oligomer which is made up of polymerized tau proteins, or the like. "Selectively collecting the complex" is not limited to collecting the complex only, but is a concept that encompasses collecting the complex with substances other than the complex also slightly included. The base plate is formed as a glass plate or the like, for example. The "information regarding the structure of the test substance" can broadly encompass the size (e.g., length), the morphology (e.g. aspect ratio), the structure (e.g., the primary structure, the secondary structure, the tertiary structure, and the quaternary structure of protein), the chemical bond, the aggregation degree, and the like.

In the method for obtaining the information of the test substance according to the present mode, the complex is selectively collected from the specimen and the collected complex is immobilized on the base plate. At this time, impurities such as substances other than the test substance contained in the specimen and the capture substance that has not formed the complex are separated from the complex and are suppressed from being transferred to the base plate. Therefore, to the base plate, substantially only the test substance is transferred and immobilized. Thus, the information regarding the structure of the test substance can be accurately obtained.

In the method for obtaining the information of the test substance according to the present mode, in the obtaining (S17, S27) of the information regarding the structure of the test substance (11), at least one of size, morphology, structure, and aggregation degree of the test substance (11) is obtained.

In the method for obtaining the information of the test substance according to the present mode, the capture substance includes a capture substance (40) for labeling the test substance (11) with fluorescence. Even when this capture substance has not formed the complex, this capture substance is suppressed from being transferred to the base plate, and thus, this capture substance can be suppressed from causing noise.

In the method for obtaining the information of the test substance according to the present mode, the capture substance includes a capture substance (30) capable of binding to a solid phase (20). Even when this capture substance has not formed the complex, this capture substance is suppressed from being transferred to the base plate, and thus, this capture substance can be suppressed from causing noise.

In the method for obtaining the information of the test substance according to the present mode, the capture substance includes a capture substance (50) capable of binding to the base plate (80). Even when this capture substance has not formed the complex, this capture substance is suppressed from being transferred to the base plate, and thus, this capture substance can be suppressed from causing noise.

In the method for obtaining the information of the test substance according to the present mode, the capture substance (40) for labeling the test substance (11) with fluorescence includes an antibody (42) labeled with a fluorescent dye (41), and in the forming (S13, S22) of the complex (60, 61), the antibody (42) labeled with the fluorescent dye (41) is caused to bind to the test substance (11). Accordingly, the base plate can be suppressed from being directly fluorescence-labeled, and thus, the information regarding the structure of the test substance can be accurately obtained.

In the method for obtaining the information of the test substance according to the present mode, after the solid phase (20) is caused to bind to the complex (60, 61) through the capture substance (30) capable of binding to the solid phase (20), the solid phase (20) is selectively separated (S14, S23) in the collecting (S14, S15, S23, S24) of the complex (60, 61) from the specimen (10). Accordingly, selectively collecting the complex from the specimen is facilitated. In addition, in the latter stage, the complex can be easily detached from the solid phase.

In this case, in the collecting (S14, S15, S23, S24) of the complex (60, 61) from the specimen (10), the complex (60, 61) is caused to be detached (S15, S24) from the solid phase (20) after the solid phase (20) is selectively separated. Accordingly, since the solid phase is not transferred to the base plate, the information regarding the structure of the test substance can be more accurately obtained.

The solid phase (20) includes a magnetic particle (21), and the solid phase (20) is selectively separated by attracting the magnetic particle (21) by magnetic force. Accordingly, the complex and the impurity can be smoothly separated from each other.

The capture substance (30) capable of binding to the solid phase (20) includes an antibody (32) which binds to the test substance (11) and a second binding substance (31) which binds to the solid phase (20), and the solid phase (20) includes a second binding partner (22) which specifically binds to the second binding substance (31). Binding between the complex (60, 61) and the solid phase (20) is realized by binding between the test substance (11) and the antibody (32) of the capture substance (30) capable of binding to the solid phase (20), and by specific binding between the second binding substance (31) and the second binding partner (22).

In this case, a combination of the second binding substance (31) and the second binding partner (22) is selected from combinations of: an antigen and an antibody thereto; a ligand and a receptor therefor; an oligonucleotide and a complementary strand thereof; and biotins including biotin and biotin analogs such as desthiobiotin and avidins including avidin and avidin analogs such as streptavidin. Accordingly, the second binding substance and the second binding partner can be stably bound to each other.

The second binding substance (31) is an anti-hapten, and the second binding partner (22) is an anti-hapten antibody. Also in this case, the second binding substance and the second binding partner can be stably bound to each other.

In this case, the second binding substance (31) is a dinitrophenyl group and the second binding partner (22) is an anti-dinitrophenyl group antibody. Accordingly, the second binding substance and the second binding partner can be easily detached from each other.

In this case, the second binding substance (31) and the second binding partner (22) bound to each other are caused to be detached from each other by use of a dinitrophenyl amino acid.

In the method for obtaining the information of the test substance according to the present mode, the capture substance includes a capture substance (50) capable of binding to the base plate (80) and a capture substance (30) capable of binding to a solid phase (20), and the capture substance (50) capable of binding to the base plate (80) and the capture substance (30) capable of binding to the solid phase (20) are different from each other. In this case, two kinds of capture substances individually bind to the test substance. If the capture substance for immobilizing the test substance onto the base plate and the capture substance for binding the test substance to the solid phase are different from each other, the latter capture substance that has not bound to the test substance can be removed during collection of the complex. Thus, the capture substance capable of binding to the base plate and not having bound to the test substance can be suppressed from being immobilized onto the base plate, and thus, immobilization of the test substance onto the base plate can be more smoothly performed.

In this case, the capture substance (50) capable of binding to the base plate (80) and the capture substance (30) capable of binding to the solid phase (20) are substantially simultaneously put into the specimen (10). Accordingly, the two capture substances can be smoothly caused to be bound to the binding site of the test substance.

In the method for obtaining the information of the test substance according to the present mode, in the collecting (S14, S15, S23, S24) of the complex (60, 61) from the specimen (10), the complex (60, 61) is separated from an impurity (13) on the basis of at least one of a difference in specific gravity, a difference in size, a difference in electrical property, and a difference in immunoreaction between the complex (60, 61) and the impurity (13). The difference in size, the difference in electrical property, and the difference in immunoreaction are, for example, those in gel filtration, electrophoresis, and immunoreaction, respectively. Accordingly, appropriate separation can be performed.

In the method for obtaining the information of the test substance according to the present mode, the capture substance (50) capable of binding to the base plate (80) includes an antibody (52) which binds to the test substance (11) and a binding substance (51) which binds to the base plate (80), and the base plate (80) includes a binding partner (81) which specifically binds to the binding substance (51). After the antibody (52) included in the capture substance (50) capable of binding to the base plate (80) is caused to bind to the test substance (11), the complex (60) is immobilized on the base plate (80) through specific binding between the binding partner (81) and the binding substance (51), in the immobilizing (S16, S26) of the complex (60) onto the base plate (80). Accordingly, the test substance can be specifically bound to the base plate not through physical adsorption but through mediation by the capture substance. Thus, the test substance can be stably immobilized on the base plate while the impurity is suppressed from being transferred to the base plate.

In this case, a combination of the binding substance (51) and the binding partner (81) is selected from combinations of: an antigen and an antibody thereto; a ligand and a receptor therefor; an oligonucleotide and a complementary strand thereof; and biotins including biotin and biotin analogs such as desthiobiotin and avidins including avidin and avidin analogs such as streptavidin. Accordingly, the binding substance and the binding partner can be stably bound to each other.

The binding substance (51) is a type of the biotins, and the binding partner (81) is a type of the avidins. Accordingly, due to high affinity, the test substance can be more stably immobilized on the base plate.

In the method for obtaining the information of the test substance according to the present mode, after the collecting of the complex (61) from the specimen (10), a capture substance (50) capable of binding to the base plate (80) is caused to bind to the test substance (11).

In the method for obtaining the information of the test substance according to the present mode, in the obtaining (S17, S27) of the information regarding the structure of the test substance (11), an image of the test substance (11) is obtained by performing image capturing of the test substance (11) on the base plate (80). Accordingly, the information regarding the structure of the test substance can be obtained on the basis of the obtained image.

In the method for obtaining the information of the test substance according to the present mode, in the collecting of the complex (60, 61) from the specimen (10), the test substance (11) and an impurity (13) are separated from each other, and the test substance (11) is a protein as a test target contained in the specimen (10) and the impurity (13) includes a protein other than the protein as the test target.

In the method for obtaining the information of the test substance according to the present mode, the test substance (11) is amyloid β. In this case, if the information regarding the structure of amyloid β is obtained, the obtained information can be helpful in diagnosis of Alzheimer's disease and determination of an administration policy, for example.

In the method for obtaining the information of the test substance according to the present mode, the specimen (10) is cerebrospinal fluid.

In the method for obtaining the information of the test substance according to the present mode, the obtaining (S17, S27) of the information regarding the structure of the test substance (11) is performed by means of a microscope.

In this case, the microscope is a fluorescence microscope, a Raman microscope, a probe microscope, or an electron microscope.

In the method for obtaining the information of the test substance according to the present mode, the obtaining (S17, S27) of the information regarding the structure of the test substance (11) is performed by means of a microscope having a resolution exceeding a diffraction limit of light. Accordingly, the information regarding the structure of the test substance can be obtained at a resolution exceeding the diffraction limit of light.

A second mode of the present invention relates to a method for obtaining information of a test substance. A method for obtaining information of a test substance according to the present mode includes: causing (S12, S21) a magnetic particle (21) to bind to a test substance (11) in a specimen (10); selectively collecting (S14, S15, S23, S24) at least the test substance (11) from the specimen (10) by use of the magnetic particle (21) bound to the test substance (11); immobilizing (S16, S26) the test substance (11) collected from the specimen (10), onto a base plate (80); and obtaining (S17, S27) information regarding a structure of the test substance (11) from the test substance (11) immobilized on the base plate (80).

In the method for obtaining the information of the test substance according to the present mode, the test substance is selectively collected from the specimen by means of a magnet, for example, and the collected test substance is immobilized on the base plate. At this time, impurities other than the test substance contained in the specimen are separated from the test substance and are suppressed from being transferred to the base plate. Thus, to the base plate, substantially only the test substance is transferred and immobilized. Thus, the information regarding the structure of the test substance can be accurately obtained.

A third mode of the present invention relates to a method for obtaining information of a test substance. A method for obtaining information of a test substance according to the present mode includes forming (S11 to S13, S21, S22) a complex (60, 61) by causing a capture substance (40) including a fluorescent dye (41) to bind to a test substance (11) in a specimen (10); selectively collecting (S14, S15, S23, S24) at least the complex (60, 61) from the specimen (10); immobilizing (S16, S26) the complex (60, 61) collected from the specimen (10), onto a base plate (80); and obtaining (S17, S27) information regarding a structure of the test substance (11) on the basis of bright spots corresponding to fluorescence emitted from a plurality of fluorescent dyes (41) each bound to the complex (60) immobilized on the base plate (80).

In the method for obtaining the information of the test substance according to the present mode, the complex is selectively collected from the specimen and the collected complex is immobilized on the base plate. At this time, substances other than the test substance contained in the specimen and impurities such as a capture substance that has not formed the complex are separated from the complex and are suppressed from being transferred to the base plate. Thus, to the base plate, substantially only the test substance is transferred and immobilized. Thus, the information regarding the structure of the test substance can be accurately obtained on the basis of the bright spots corresponding to fluorescence emitted from the fluorescent dyes.

A fourth mode of the present invention relates to a method for obtaining information of a test substance. A method for obtaining information of a test substance according to the present mode includes: separating (S14, S23) a test substance (11) and an impurity (13) in a specimen (10) from each other; immobilizing (S16, S26) the test substance (11) separated from the impurity (13), onto a base plate (80); and obtaining (S17, S27) information regarding a structure of the test substance (11) immobilized on the base plate (80).

In the method for obtaining the information of the test substance according to the present mode, the test substance and the impurity are separated from each other, and the separated test substance is immobilized on the base plate. At this time, substances other than the test substance contained in the specimen and impurities such as a capture substance used in the separation are separated from the test substance and are suppressed from being transferred to the base plate. Thus, to the base plate, substantially only the test substance is transferred and immobilized. Thus, the information regarding the structure of the test substance can be accurately obtained.

In the method for obtaining the information of the test substance according to the present mode, the test substance (11) is a protein as a test target contained in the specimen (10), and the impurity (13) includes a protein other than the protein as the test target.

In the method for obtaining the information of the test substance according to the present mode, the specimen (10) is cerebrospinal fluid.

According to the present invention, information regarding the structure of a test substance can be accurately obtained.

BRIEF DESCRIPTION OF THE DRAWINGS

FIG. 15 is a diagram showing an example of a screen displayed on a display unit in the information obtaining step according to Embodiments 1 to 4;

FIG. 16A shows super-resolution images obtained through the procedure of verification of Embodiment 1;

FIG. 16B shows fluorescence images obtained through the procedure of verification of Embodiment 1;

FIG. 16C is a graph showing the relationship between the number of bright spots on the fluorescence images obtained in the verification of Embodiment 1 and the concentration of the test substance;

FIG. 17A shows a super-resolution image obtained through the procedure of verification of Comparative Example;

FIG. 17B shows fluorescence images obtained through the procedure of verification of Comparative Example;

FIG. 17C is a graph showing the relationship between the number of bright spots on the fluorescence images obtained in the verification of Comparative Example and the concentration of the test substance;

DETAILED DESCRIPTION OF THE PREFERRED EMBODIMENTS

Embodiments 1 to 4 shown below indicate embodiments of the present disclosure. A specimen is a liquid taken from a living body and is CSF (cerebrospinal fluid), blood, plasma, interstitial fluid, urine, or the like, for example. A test substance is a cell, a polypeptide, a protein, a nucleic acid, an exosome, a carbohydrate chain, or the like, and in the information obtaining method of Embodiments 1 to 4, a multimer is appropriate. The test substance is an amyloid $\beta$ oligomer which is made up of polymerized amyloid $\beta$ monomers, a tau oligomer which is made up of polymerized tau proteins, or the like, for example. In Embodiments 1 to 4, the specimen is CSF, and the test substance is amyloid $\beta$.

Embodiment 1

Figure 1:
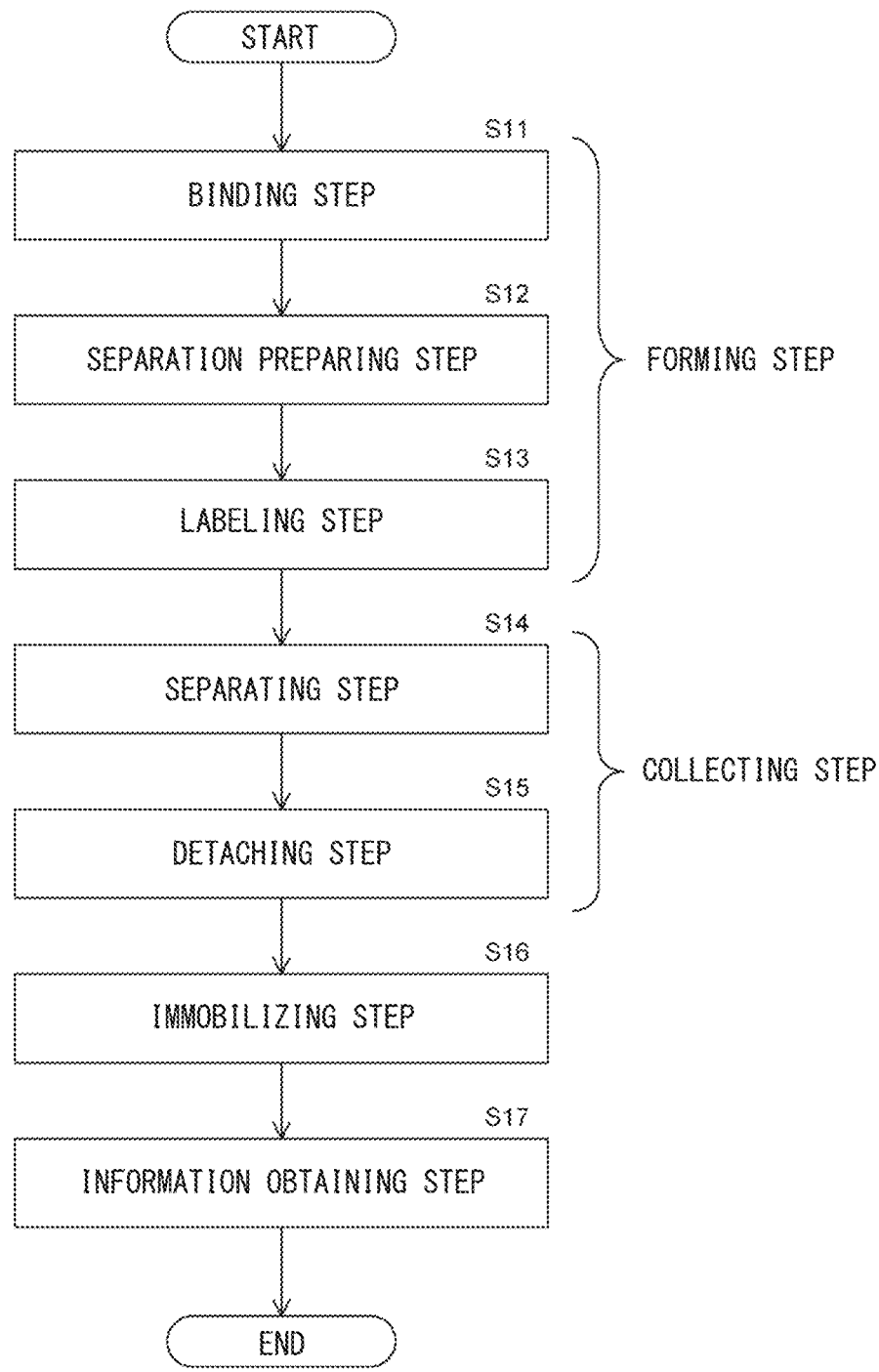
FIG. 1 is a flow chart showing an information obtaining method according to Embodiment 1.

As shown in FIG. 1, an information obtaining method of Embodiment 1 includes process steps of steps S11 to S17. Steps S11 to S16 may be manually performed by an operator or may be automatically performed by a processing apparatus. The information obtaining step of step S17 may be performed by the operator by use of a microscope, or may be automatically performed by a detection apparatus. The detection apparatus which automatically performs the information obtaining step of step S17 will be described later with reference to FIG. 18.

Figure 2B:
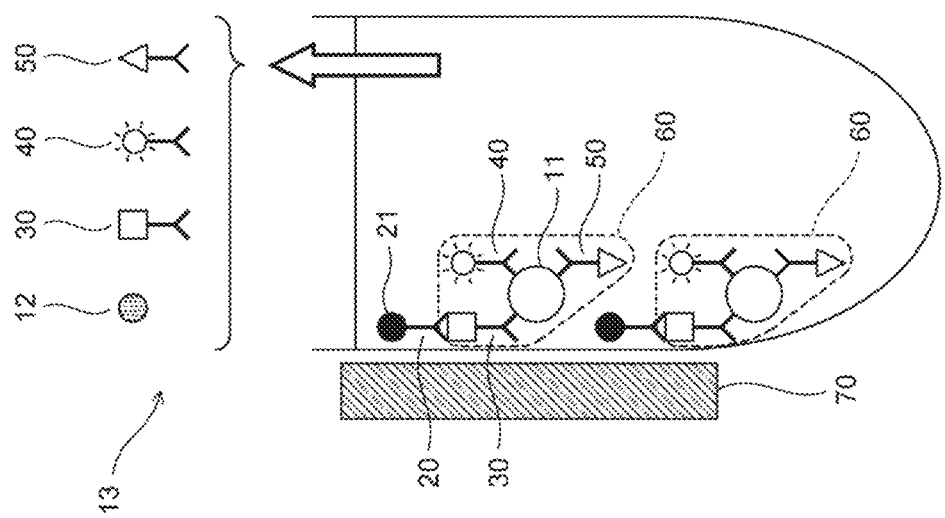
FIG. 2B is a schematic diagram showing a separating step according to Embodiment 1.
Figure 2A:
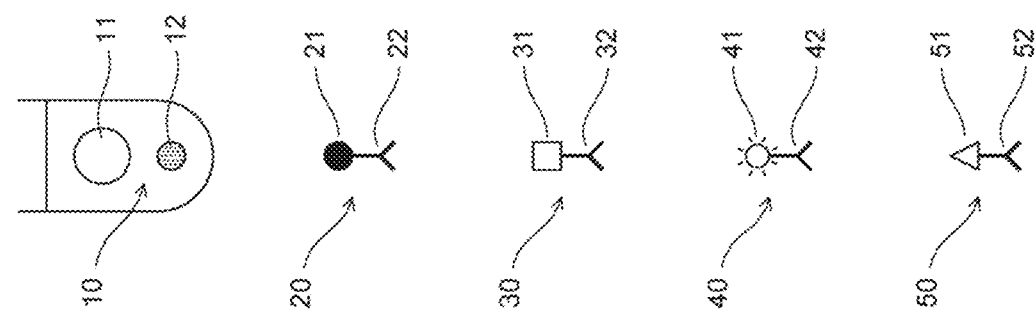
FIG. 2A is a schematic diagram showing a binding step, a separation preparing step, and a labeling step according to Embodiment 1.

As shown in FIG. 2A, a specimen 10 contains a test substance 11 and an impurity 12. The impurity 12 is a substance which is other than the test substance 11 and which is not necessary. The impurity 12 is a protein other than the test substance 11, for example. In each step shown in FIG. 1, a solid phase 20, a second capture substance 30, a third capture substance 40, and a first capture substance 50 are used. In the following, each step shown in FIG. 1 is described with reference to FIG. 2A to FIG. 4. In a forming step composed of steps S11 to S13, steps S11 to S13 are simultaneously performed. In the forming step, each capture substance is bound to the test substance 11 in the specimen 10, whereby a complex 60 is formed. In a collecting step composed of steps S14 and S15, the complex 60 is selectively collected from the specimen 10.

In the binding step of step S11, the first capture substance 50 is bound to the test substance 11. As shown in FIG. 2A, the first capture substance 50 is a substance capable of binding to a base plate 80 shown in FIG. 4, and includes a binding substance 51 and an antibody 52 having the binding substance 51 bound thereto. The binding substance 51 specifically binds to a binding partner 81 of the base plate 80 described later, and the antibody 52 specifically binds to the test substance 11. As a result of the antibody 52 binding to the test substance 11, the first capture substance 50 and the test substance 11 are bound to each other.

In a separation preparing step of step S12, the solid phase 20 is bound to the complex 60 through the second capture substance 30. As shown in FIG. 2A, the solid phase 20 includes a magnetic particle 21 and a second binding partner 22 having the magnetic particle 21 bound thereto. The second capture substance 30 includes a second binding substance 31 and an antibody 32 having the second binding substance 31 bound thereto. The second binding partner 22 specifically binds to the second binding substance 31 and the antibody 32 specifically binds to the test substance 11. The second binding partner 22 and the second binding substance 31 are bound to each other and the antibody 32 and the test substance 11 are bound to each other, whereby the solid phase 20 and the complex 60 are bound to each other.

As described above, if the specific binding of the complex 60 to the solid phase 20 is performed through the second capture substance 30 capable of binding to the solid phase 20, the complex 60 can be detached from the solid phase 20 in a detaching step in the latter stage. In addition, the solid phase 20 and the test substance 11 can be stably bound to each other.

A combination of the second binding substance 31 and the second binding partner 22 is selected from combinations of: an antigen and an antibody thereto; a ligand and a receptor therefor; an oligonucleotide and a complementary strand thereof; and biotins including biotin and biotin analogs such as desthiobiotin and avidins including avidin and avidin analogs such as streptavidin. Then, the second binding substance 31 and the second binding partner 22 can be stably bound to each other. Examples of the combination of a ligand and a receptor therefor include combinations of: an enzyme and a substrate therefor; and a signal substance such as a hormone or a neurotransmitter and a receptor therefor. Alternatively, a combination in which the second binding substance 31 is an anti-hapten and the second binding partner 22 is an anti-hapten antibody may be employed. Also in this case, the second binding substance 31 and the second binding partner 22 can be stably bound to each other.

In Embodiment 1, the second binding substance 31 is a dinitrophenyl group and the second binding partner 22 is an anti-dinitrophenyl group antibody. In this case, if a dinitrophenyl amino acid is used as a releaser described later, the second binding substance 31 and the second binding partner 22 bound to each other can be easily detached from each other.

In Embodiment 1, the first capture substance 50 and the second capture substance 30 are configured to be different from each other, but the configuration is not limited thereto. For example, instead of the first capture substance 50 and the second capture substance 30, the binding substance 51 and the second binding substance 31 are bound to a single antibody, whereby another capture substance may be configured. However, in this case, in a separating step, not the test substance 11 alone but the other capture substance that does not have the test substance 11 bound thereto is also taken out together with the test substance 11. Thus, in an immobilizing step, the other capture substance that does not have the test substance 11 bound thereto is immobilized to the binding partner 81 of the base plate 80. Thus, the test substance 11 becomes less likely to be bound to the binding partner 81, and the efficiency of immobilizing the test substance 11 to the base plate 80 is decreased. Therefore, in order to smoothly perform immobilization of the test substance 11 onto the base plate 80, it is preferable that the first capture substance 50 and the second capture substance 30 are configured to be different from each other and individually bound to the test substance 11.

In a labeling step of step S13, the third capture substance 40 is bound to the test substance 11. As shown in FIG. 2A, the third capture substance 40 includes a fluorescent dye 41 which is a fluorescent label, and an antibody 42 labeled with the fluorescent dye 41. The antibody 42 specifically binds to the test substance 11. As a result of the antibody 42 and the test substance 11 binding to each other, a fluorescent label is provided to the test substance 11.

In Embodiment 1, at least portions of the epitopes of the antibody 52 of the first capture substance 50, the antibody 32 of the second capture substance 30, and the antibody 42 of the third capture substance 40 overlap one another, and steps S11 to S13 are simultaneously performed. In such a case where at least portions of the epitopes of the respective antibodies overlap one another, it is preferable that steps S11 to S13 are performed simultaneously. More specifically, a step of mixing the first capture substance 50 into the specimen 10 in step S11, a step of mixing the second capture substance 30 into the specimen 10 in step S12, and a step of mixing the third capture substance 40 into the specimen 10 in step S13 are preferably performed simultaneously.

For example, if the second capture substance 30 is mixed into the specimen 10 before the first capture substance 50 is mixed into the specimen 10, the binding site in the test substance 11 is occupied by the second capture substance 30, which could hinder smooth binding of the first capture substance 50 to the test substance 11. If the mixing timings are different in such a manner, the substances mixed later are less likely to bind to the test substance 11. By simultaneously mixing the first capture substance 50, the second capture substance 30, and the third capture substance 40 into the specimen 10, each substance is allowed to smoothly bind to the test substance 11.

When the epitopes of the respective antibodies do not overlap one another, it is possible that steps S11 to S13 are not simultaneously performed, and the order of steps S11 to S13 is also not limited to the order shown in FIG. 1.

At the time point when steps S11 to S13 have ended, as shown in FIG. 2A, the first capture substance 50, the second capture substance 30, and the third capture substance 40 are bound to the test substance 11 in the specimen 10 in the container, to form the complex 60, whereby a state in which the solid phase 20 is bound to the complex 60 is established.

In the separating step of step S14, the solid phase 20 is selectively separated, whereby the test substance 11 is separated from the specimen 10. Specifically, by the complex 60 being separated from impurities 13, the test substance 11 is taken out from the specimen 10. The impurities 13 of Embodiment 1 include: the impurity 12; and the capture substances 30, 40, and 50 which have not formed the complex 60, as shown in FIG. 2B.

As shown in FIG. 2B, the separation of the complex 60 from the impurities 13 in the separating step is performed by use of a magnet 70, for example. When the magnet 70 is brought close to the container, the magnetic particle 21 is attracted by the magnetic force to the inner wall of the container at which the magnet 70 is located. At this time, since the magnetic particle 21 and the test substance 11 are integrated with each other, the test substance 11 is also attracted to the inner wall of the container, together with the magnetic particle 21. In this state, the liquid in the container is removed. The removed liquid contains the impurities 13. Thus, the test substance 11 and the impurities 13 are separated from each other, and the test substance 11 is taken out from the specimen 10.

In Embodiment 1, before the separating step, the step of causing the first capture substance 50 to bind to the test substance 11 is performed. Thus, in addition to the separation of the impurity 12, the first capture substance 50 that has not bound to the test substance 11 can be separated from the test substance 11, in the separating step. Accordingly, the first capture substance 50 that has not bound to the test substance 11 can be suppressed from being transferred to the base plate 80 in the immobilizing step of step S16. Similarly, before the separating step, the steps of causing the second capture substance 30 and the third capture substance 40 to bind to the test substance 11 are performed. Thus, in addition to the separation of the impurity 12, the second capture substance 30 and the third capture substance 40 that have not bound to the test substance 11 can be separated from the test substance 11 in the separating step. Accordingly, the second capture substance 30 and the third capture substance 40 that have not bound to the test substance 11 can be suppressed from being transferred to the base plate 80 in the immobilizing step of step S16.

It should be noted that, in a case where the step of causing the first capture substance 50 to bind to the test substance 11 is performed after the separating step, it is preferable to further perform a step of removing the first capture substance 50 that has not bound to the test substance 11. The "separation in the separating step" is not limited to separation of the complex 60 only, but is a concept that encompasses separation of the complex 60 with substances other than the complex 60 slightly included.

In Embodiment 1, on the basis of a difference in immunoreaction, i.e., on the basis of the specific binding between the antibody 32 of the second capture substance 30 and the test substance 11 through antigen-antibody reaction, the solid phase 20 is selectively collected in the separating step, whereby the test substance 11 and the impurities 13 are separated from each other. However, not limited thereto, the method for separating the test substance 11 and the impurity 12 from each other may be any separating method based on at least one of a difference in specific gravity, a difference in size, a difference in electrical property, and a difference in immunoreaction between the complex 60 and the impurities 13. Specifically, the separating method may be gel filtration, electrophoresis, immunoreaction, or the like. Then, the separation can be performed appropriately. If a difference in immunoreaction is used as described above, the binding specificity between the complex 60 and the solid phase 20 is enhanced, and thus, the test substance 11 can be more accurately separated from the impurities 13.

The separation of the test substance 11 is preferably performed by use of the solid phase 20 as described above. The solid phase 20 preferably includes the magnetic particle 21 as described above, and preferably, the magnetic particle 21 bound to the test substance 11 is attracted by means of the magnet 70, to separate the test substance 11. By attracting the magnetic particle 21 by means of the magnet 70, the separation between the test substance 11 and the impurities 13 can be smoothly performed.

Figure 3B:
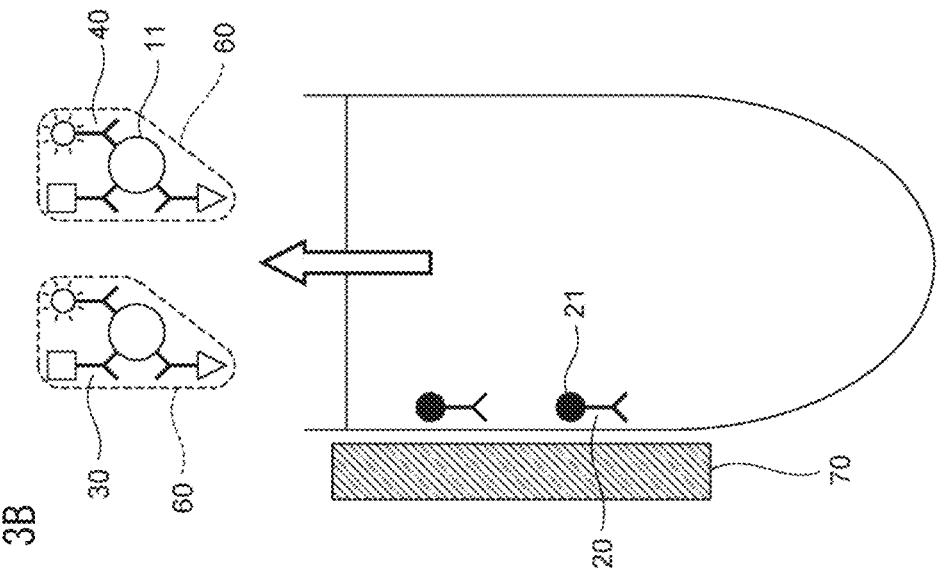
FIG. 3B is a schematic diagram showing the detaching step according to Embodiment 1.
Figure 3A:
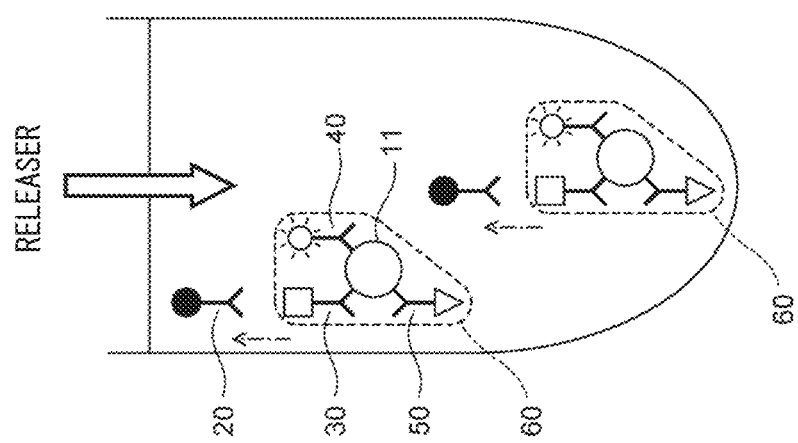
FIG. 3A is a schematic diagram showing a detaching step according to Embodiment 1.

In the detaching step of step S15, the complex 60 is detached from the solid phase 20. Specifically, as shown in FIG. 3A, the releaser is mixed into the liquid containing the separated complex 60, whereby the solid phase 20 is detached from the complex 60. Accordingly, the solid phase 20 is released in the liquid. Then, as shown in FIG. 3B, the magnet 70 is brought close to the container, and the solid phase 20 is attracted by means of the magnet 70 to the inner wall of the container at which the magnet 70 is located. In this state, the liquid in the container is taken out. The liquid that has been taken out contains the complex 60. In this manner, the complex 60 is detached from the solid phase 20.

Since the solid phase 20 is detached, occurrence of noise caused by the solid phase 20 bound to the test substance 11, other substances nonspecifically bound to the solid phase 20, and the like is suppressed in observation of the test substance 11.

The detachment between the complex 60 and the solid phase 20 may be realized on the basis of immunological separation due to competitive reaction, or may be realized on the basis of chemical separation by use of a reducing agent, for example. In Embodiment 1, as shown in FIG. 3A, as a result of the second binding partner 22 and the second binding substance 31 being detached from each other, the complex 60 and the solid phase 20 are detached from each other. However, the detachment between the complex 60 and the solid phase 20 is not limited thereto, and it is sufficient that, at any portion that connects the magnetic particle 21 and the complex 60 to each other, the complex 60 side and the solid phase 20 side are detached from each other.

Figure 4:
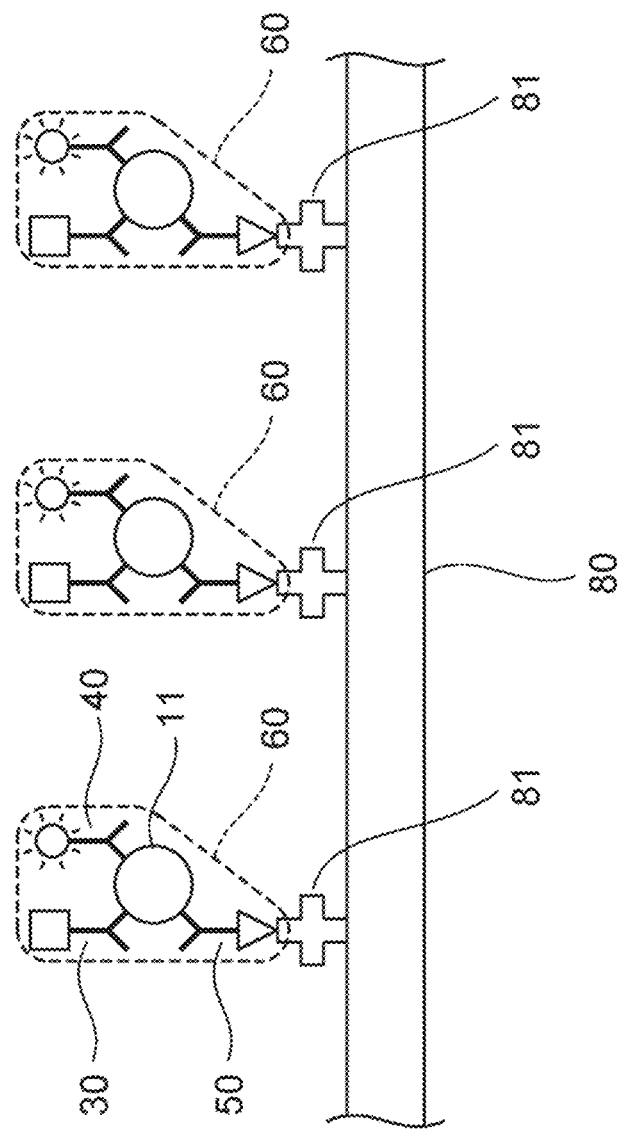
FIG. 4 is a schematic diagram showing an immobilizing step according to Embodiment 1.

In the immobilizing step of step S16, as shown in FIG. 4, the first capture substance 50 is bound to the base plate 80, whereby the test substance 11 is immobilized on the base plate 80. The base plate 80 is formed as a glass plate or the like, for example. The base plate 80 includes the binding partner 81 which specifically binds to the binding substance 51 of the first capture substance 50. In the immobilizing step, through specific binding between the binding partner 81 and the binding substance 51, the test substance 11 is immobilized on the base plate 80. Thus, if the test substance 11 is specifically bound to the base plate 80 not through physical adsorption but through mediation by the first capture substance 50, the test substance 11 can be stably immobilized on the base plate 80 while transfer of the impurities 13 to the base plate 80 is further suppressed.

The combination of the binding substance 51 and the binding partner 81 is selected from combinations of: an antigen and an antibody thereto; a ligand and a receptor therefor; an oligonucleotide and a complementary strand thereof; and biotins including biotin and biotin analogs such as desthiobiotin and avidins including avidin and avidin analogs such as streptavidin. Then, the binding substance 51 and the binding partner 81 can be stably bound to each other. Examples of the combination of a ligand and a receptor therefor include combinations of: an enzyme and a substrate therefor; a signal substance such as a hormone or a neurotransmitter, and a receptor therefor. In Embodiment 1, the binding substance 51 is a type of the biotins, and the binding partner 81 is a type of the avidins. In this case, due to high affinity between the binding substance 51 and the binding partner 81, the test substance 11 can be more stably immobilized on the base plate 80.

In Embodiment 1, the labeling step is performed before the immobilizing step. Thus, direct attachment of the third capture substance 40 to the base plate 80 is suppressed, and information regarding the structure of the test substance 11 can be accurately obtained in an information obtaining step described later. In addition, after the complex 60 is detached from the solid phase 20, the first capture substance 50 bound to the complex 60 which has been detached from the solid phase 20 is bound to the base plate 80, whereby the test substance 11 is immobilized on the base plate 80. Therefore, since the solid phase 20 is not transferred to the base plate 80, information regarding the structure of the test substance 11 can be accurately obtained.

In the information obtaining step of step S17, information regarding the structure of the test substance 11 is obtained from the test substance 11 immobilized on the base plate 80. It should be noted that "information regarding the structure of the test substance" is a concept that broadly encompasses the size, the morphology, the structure, the chemical bond, the aggregation degree, and the like of the test substance 11. Details of the information obtaining step are described later with reference to FIG. 12.

In Embodiment 1, the test substance 11 is separated from the specimen 10, and the separated test substance 11 is immobilized on the base plate 80. Thus, the impurities 13 are suppressed from being transferred to the base plate 80, and substantially only the test substance 11 is transferred to the base plate 80 and immobilized thereon. Therefore, information regarding the structure of the test substance 11 can be accurately obtained. Since the impurities 13 are suppressed from being transferred to the base plate 80, even when the concentration of the test substance 11 is low, a signal derived from the test substance 11 is less likely to be obstructed by signals derived from the impurities 13. Accordingly, information regarding the structure of the test substance 11 can be highly accurately obtained while influence of the impurities 13 is suppressed.

Information regarding the structure of the test substance 11 changes depending on the disease progression and the like, and thus, is useful in pathological diagnosis, determination of an administration policy, and the like. For example, when the test substance 11 is amyloid β, information regarding the structure of amyloid β can be helpful in diagnosis of Alzheimer's disease and determination of an administration policy therefor. According to Embodiment 1, since the impurities 13 are removed, even when the concentration of amyloid β is low, information regarding the structure of amyloid β can be highly accurately obtained. Thus, even in a case where the concentration of amyloid β is low such as during the early stages of Alzheimer's disease, the obtained information regarding the structure can be helpful in diagnosis of disease progression.

Embodiment 2

Figure 5:
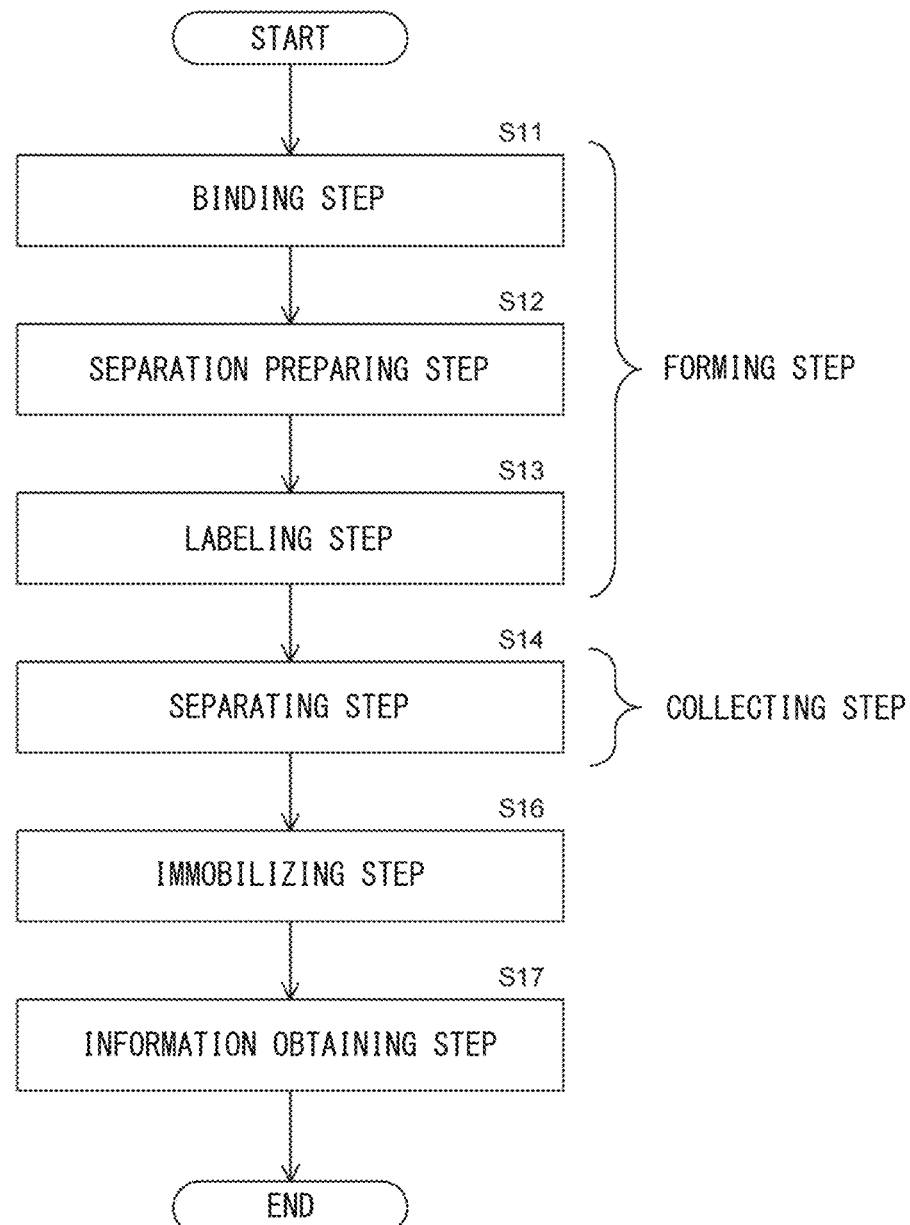
FIG. 5 is a flow chart showing an information obtaining method according to Embodiment 2.

As shown in FIG. 5, in Embodiment 2, compared with Embodiment 1, the detaching step of step S15 is omitted from the flow chart shown in FIG. 1. That is, in Embodiment 2, after steps S11 to S13 are performed as in Embodiment 1, steps S16 and S17 are performed, without the detaching step being performed. The collecting step of Embodiment 2 is configured as the separating step of step S14.

Figure 6:
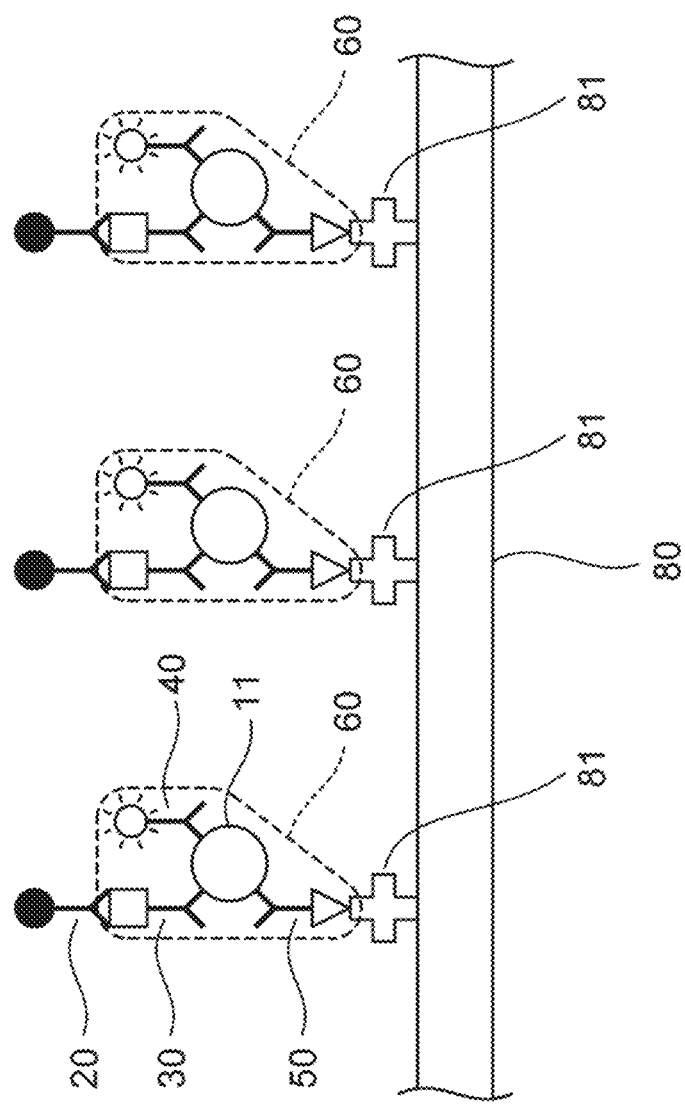
FIG. 6 is a schematic diagram showing an immobilizing step according to Embodiment 2.

In Embodiment 2, as a result of steps S11 to S14 being performed, the test substance 11 and the impurities 13 are separated from each other and the test substance 11 is taken out from the specimen 10, as in Embodiment 1 and as shown in FIG. 2B. Subsequently, in Embodiment 2, the immobilizing step of step S16 is performed. In the immobilizing step of step S16, as shown in FIG. 6, the first capture substance 50 is bound to the base plate 80, whereby the test substance 11 is immobilized on the base plate 80. At this time, different from Embodiment 1, the test substance 11 has the solid phase 20 bound thereto. Then, in the information obtaining step of step S17, as in Embodiment 1, information regarding the structure of the test substance 11 is obtained from the test substance 11 immobilized on the base plate 80.

Also in Embodiment 2, as in Embodiment 1, the impurities 13 are suppressed from being transferred to the base plate 80, and substantially only the test substance 11 is transferred to the base plate 80 and immobilized thereon. Thus, information regarding the structure of the test substance 11 can be accurately obtained. In Embodiment 2, since the step for removing the solid phase 20 is omitted, the test substance 11 is not removed in the step for removing the solid phase 20. It should be noted that in a case where the detaching step is omitted, the magnetic particle 21 may be bound to the test substance 11 not through the second capture substance 30. For example, an antibody bound to the magnetic particle is bound to the test substance 11, whereby the magnetic particle 21 may be bound to the test substance 11. Alternatively, the magnetic particle 21 may be directly bound to the test substance 11.

Embodiment 3

Figure 7:
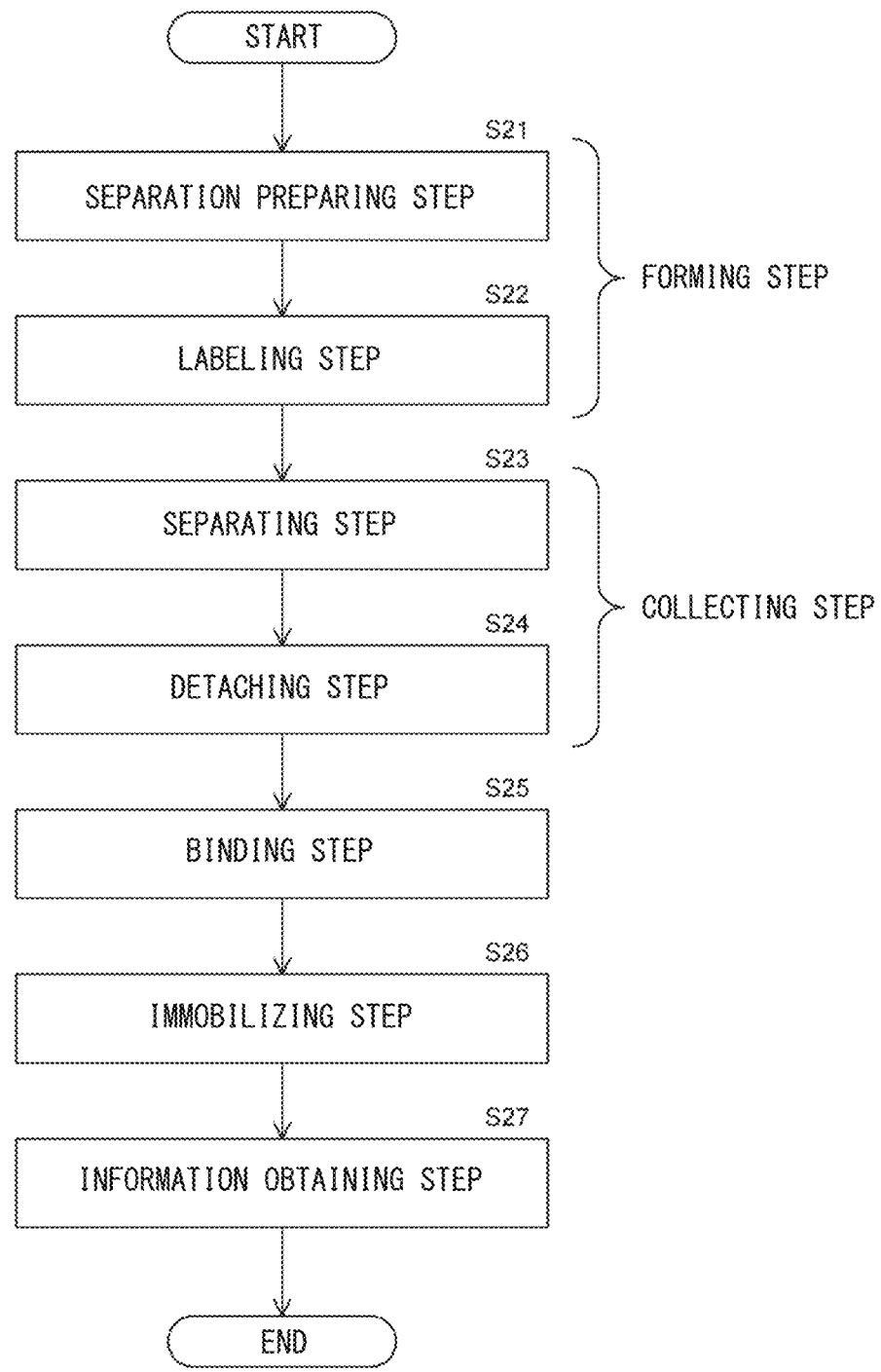
FIG. 7 is a flow chart showing an information obtaining method according to Embodiment 3.

As shown in FIG. 7, in Embodiment 3, compared with Embodiment 1, the binding step is performed between the detaching step and the immobilizing step in the flow chart shown in FIG. 1. That is, in Embodiment 3, after the separation preparing step, the labeling step, the separating step, and the detaching step are performed, the binding step is performed. In the forming step composed of steps S21 and S22, steps S21 and S22 are simultaneously performed. In the forming step, each capture substance is bound to the test substance 11 in the specimen 10, to form a complex 61. In the collecting step composed of steps S23 and S24, the complex 61 is selectively collected from the specimen 10.

Figure 8B:
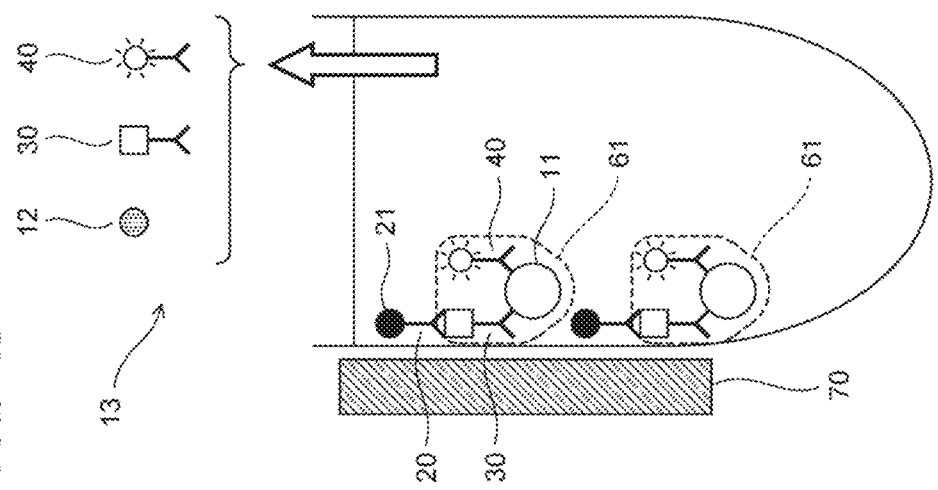
FIG. 8B is a schematic diagram showing a separating step according to Embodiment 3.
Figure 8A:
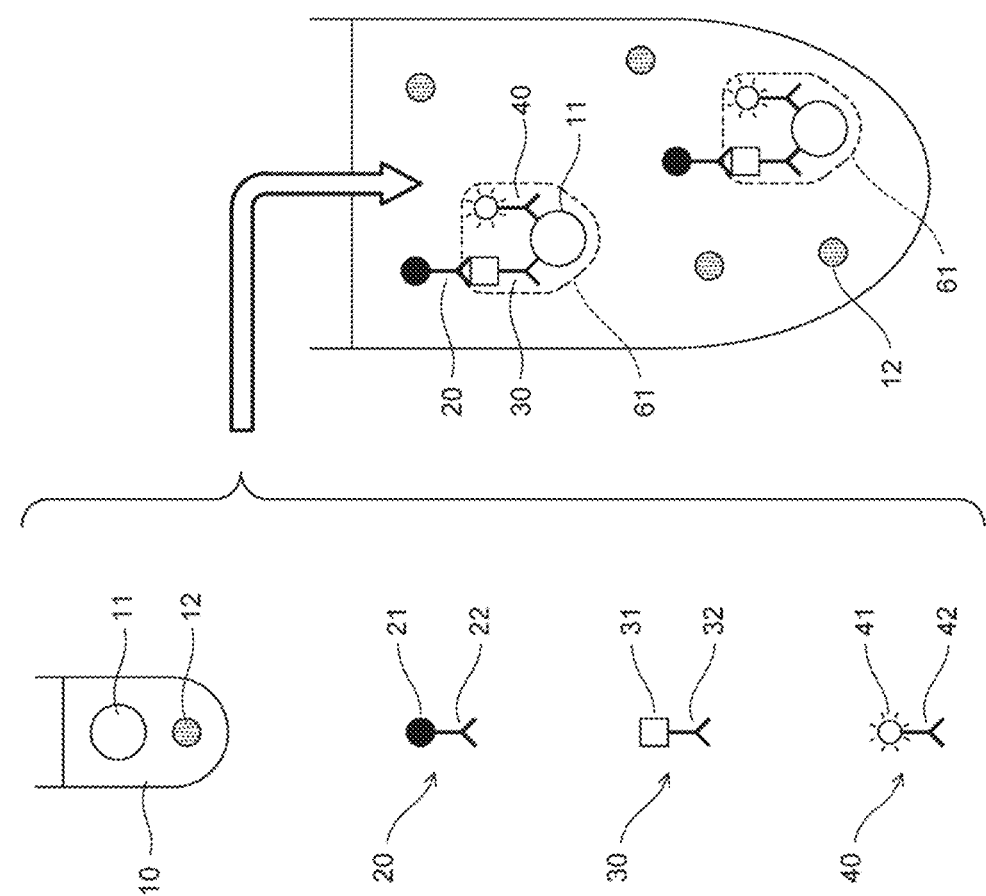
FIG. 8A is a schematic diagram showing a separation preparing step and a labeling step according to Embodiment 3.

In the separation preparing step of step S21, as shown in FIG. 8A, the solid phase 20 is bound to the test substance 11 through the second capture substance 30. Binding between the solid phase 20 and the test substance 11 is the same as that in Embodiment 1. In the labeling step of step S22, as shown in FIG. 8A, the third capture substance 40 is bound to the test substance 11. Binding between the third capture substance 40 and the test substance 11 is the same as that in Embodiment 1.

In FIG. 7, steps S21 and S22 are arranged in this order for convenience, but in actuality, steps S21 and S22 are simultaneously performed. It should be noted that it is possible that steps S21 and S22 are not simultaneously performed, and the order of steps S21 and S22 may be the reverse of the order shown in FIG. 7. However, in order to cause the second capture substance 30 and the third capture substance 40 to smoothly bind to the test substance 11, it is preferable that steps S21 and S22 are simultaneously performed.

At the time point when steps S21 and S22 have ended, as shown in FIG. 8A, in the specimen 10 in the container, the second capture substance 30 and the third capture substance 40 are bound to the test substance 11, to form the complex 61, whereby a state in which the solid phase 20 is bound to the complex 61 is established.

In the separating step of step S23, the solid phase 20 is selectively separated, whereby the test substance 11 is separated from the specimen 10. Specifically, by the complex 61 being separated from the impurities 13, the test substance 11 is taken out from the specimen 10. The impurities 13 of Embodiment 3 include: the impurity 12; and the capture substances 30 and 40 which have not formed the complex 61, as shown in FIG. 8B. As shown in FIG. 8B, the separation of the test substance 11 from the impurities 13 in the separating step is performed by use of the magnet 70, for example, as in Embodiment 1.

Figure 9C:
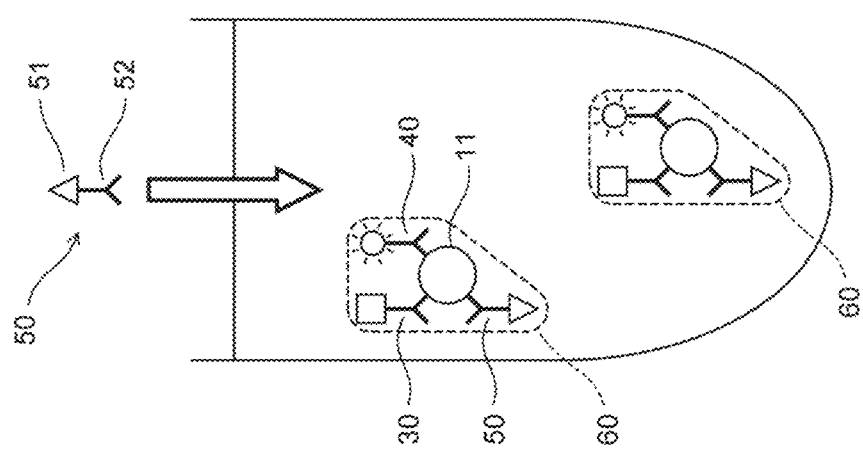
FIG. 9C is a schematic diagram showing a binding step according to Embodiment 3.
Figure 9B:
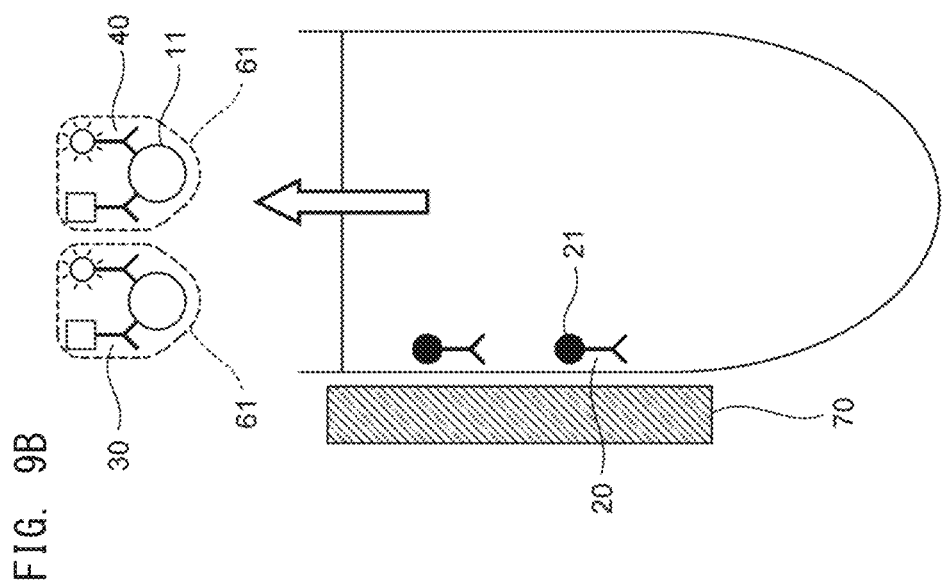
FIG. 9B is a schematic diagram showing the detaching step according to Embodiment 3.
Figure 9A:
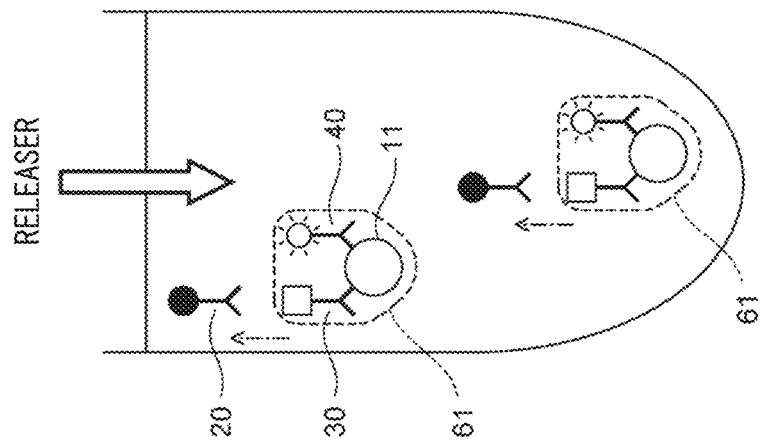
FIG. 9A is a schematic diagram showing a detaching step according to Embodiment 3.

In the detaching step of step S24, the complex 61 is detached from the solid phase 20. Specifically, as shown in FIG. 9A, a releaser is mixed into the liquid containing the separated complex 61, whereby the solid phase 20 is detached from the complex 61. Then, as shown in FIG. 9B, the solid phase 20 is attracted by means of the magnet 70 to the inner wall of the container at which the magnet 70 is located. In this state, the liquid in the container is taken out. The liquid that has been taken out contains the complex 61.

In this manner, the complex 61 is detached from the solid phase 20. Since the solid phase 20 is detached, occurrence of noise caused by the solid phase 20 bound to the test substance 11, other substances nonspecifically bound to the solid phase 20, and the like can be suppressed in observation of the test substance 11.

In the binding step of step S25, the first capture substance 50 is bound to the test substance 11. As shown in FIG. 9C, the first capture substance 50 is mixed into the liquid containing the test substance 11 taken out in the detaching step. As a result of the antibody 52 and the test substance 11 binding to each other, the first capture substance 50 and the test substance 11 are bound to each other, whereby the complex 60 is generated. It should be noted that the binding step may be performed between the separating step and the detaching step.

In the immobilizing step of step S26, as in Embodiment 1, the first capture substance 50 is bound to the base plate 80, whereby the test substance 11 is immobilized on the base plate 80 as shown in FIG. 4.

Also in Embodiment 3, as in Embodiment 1, the impurities 13 are suppressed from being transferred to the base plate 80, and substantially only the test substance 11 is transferred to the base plate 80 and immobilized thereon. Thus, information regarding the structure of the test substance 11 can be accurately obtained. After the complex 61 is detached from the solid phase 20, the first capture substance 50 is bound to the test substance 11 detached from the solid phase 20, and the test substance 11 is immobilized on the base plate 80 through the first capture substance 50. Therefore, since the solid phase 20 is not transferred to the base plate 80, information regarding the structure of the test substance 11 can be accurately obtained.

Embodiment 4

Figure 10:
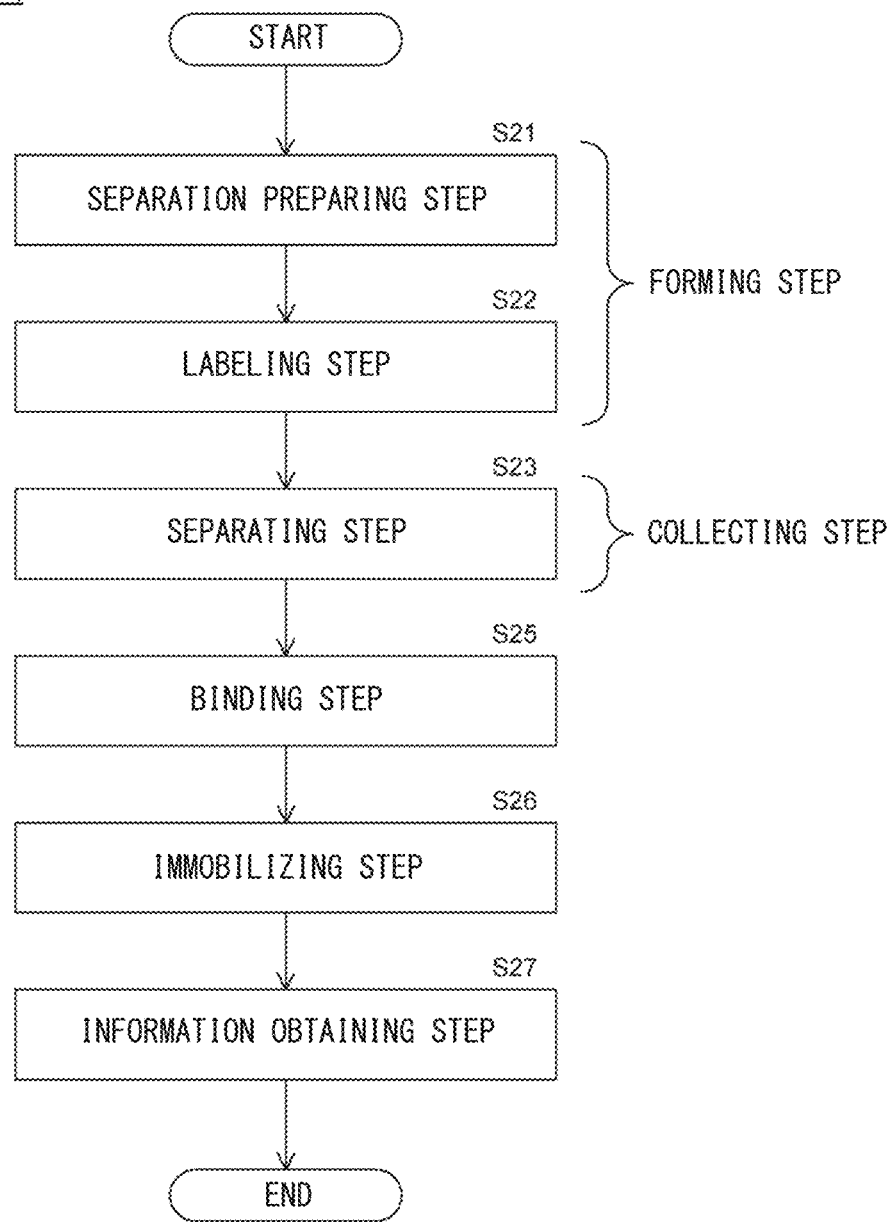
FIG. 10 is a flow chart showing an information obtaining method according to Embodiment 4.

As shown in FIG. 10, in Embodiment 4, compared with Embodiment 3, the detaching step of step S24 is omitted from the flow chart shown in FIG. 7. That is, in Embodiment 4, as in Embodiment 3, after steps S21 to S23 are performed, steps S25 to S27 are performed, without the detaching step being performed. The collecting step of Embodiment 4 is configured as the separating step of step S23.

Figure 11:
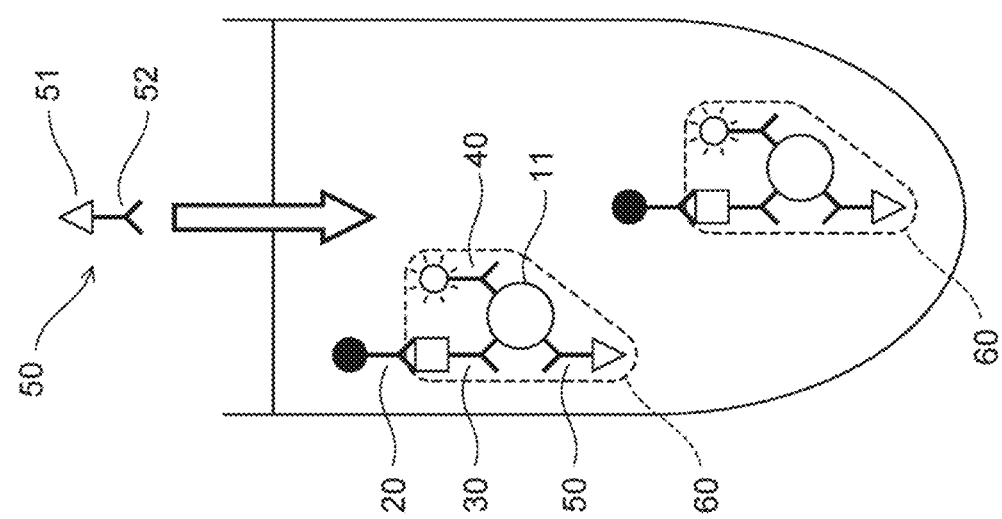
FIG. 11 is a schematic diagram showing a binding step according to Embodiment 4.

In Embodiment 4, as a result of steps S21 to S23 being performed, the test substance 11 and the impurities 13 are separated from each other, whereby the test substance 11 is taken out from the specimen 10, as in Embodiment 3 and as shown in FIG. 8B. Subsequently, in Embodiment 4, the binding step of step S25 is performed. In the binding step of step S25, as shown in FIG. 11, the first capture substance 50 is mixed into the liquid containing the complex 61 separated in the separating step. As a result of the antibody 52 and the test substance 11 binding to each other, the first capture substance 50 and the test substance 11 are bound to each other, whereby the complex 60 is generated. In the immobilizing step of step S26, as shown in FIG. 6, the first capture substance 50 is bound to the base plate 80, whereby the test substance 11 is immobilized on the base plate 80. Then, in the information obtaining step of step S27, as in Embodiment 3, information regarding the structure of the test substance 11 is obtained from the test substance 11 immobilized on the base plate 80.

Also in Embodiment 4, as in Embodiment 3, the impurities 13 are suppressed from being transferred to the base plate 80, and substantially only the test substance 11 is transferred to the base plate 80 and immobilized thereon. Thus, information regarding the structure of the test substance 11 can be accurately obtained. In addition, in Embodiment 4, since the step for removing the solid phase 20 is omitted, the test substance 11 is not removed in the step for removing the solid phase 20.

<Information Obtaining Step>

Next, details of the information obtaining step of Embodiments 1 to 4 are described.

The information obtaining step includes a step of measuring the test substance 11 on the base plate 80 by means of a super-resolution fluorescence microscope having a resolution exceeding the diffraction limit of light. When a microscope having a resolution exceeding the diffraction limit of light is used, information regarding the structure of the test substance 11 can be obtained at a resolution exceeding the diffraction limit of light. It should be noted that the information obtaining step may be automatically performed by a detection apparatus 100 described later with reference to FIG. 18.

Figure 12:
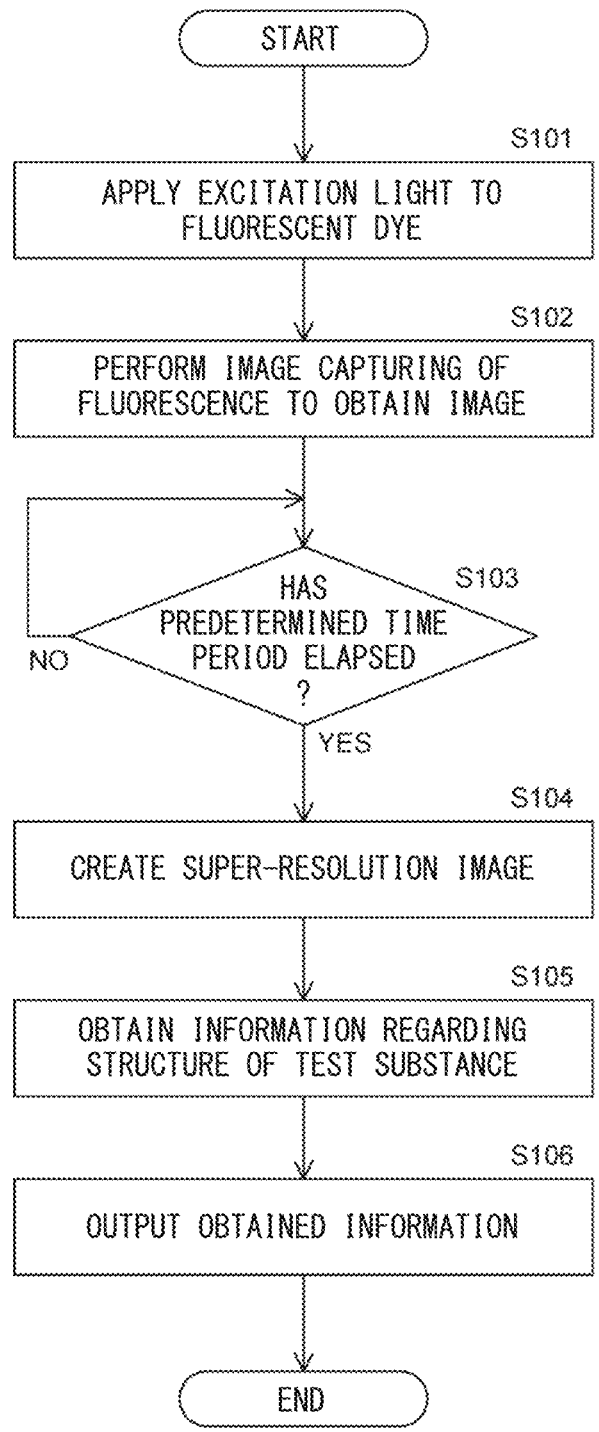
FIG. 12 is a flow chart showing an information obtaining step according to Embodiments 1 to 4.
Figure 13A:
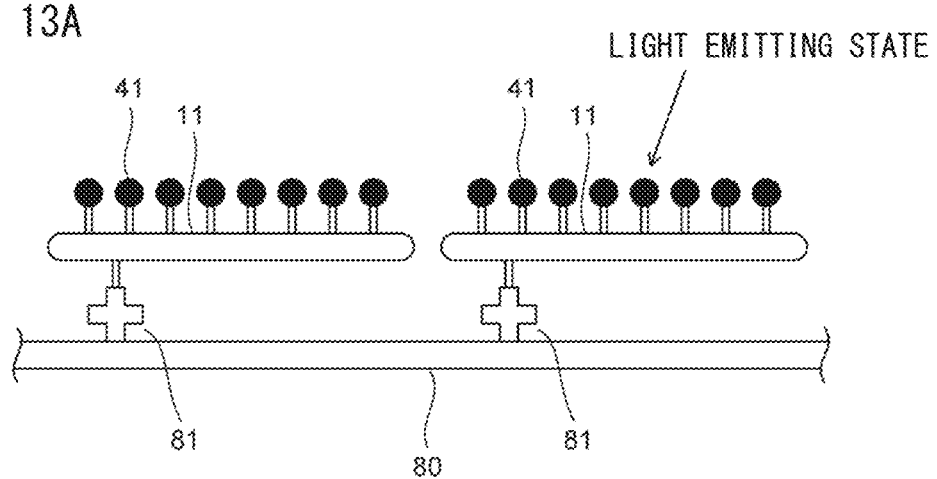
FIG. 13A is a schematic diagram showing that all fluorescent dyes are in a light emitting state in the information obtaining step according to Embodiments 1 to 4.
Figure 13B:
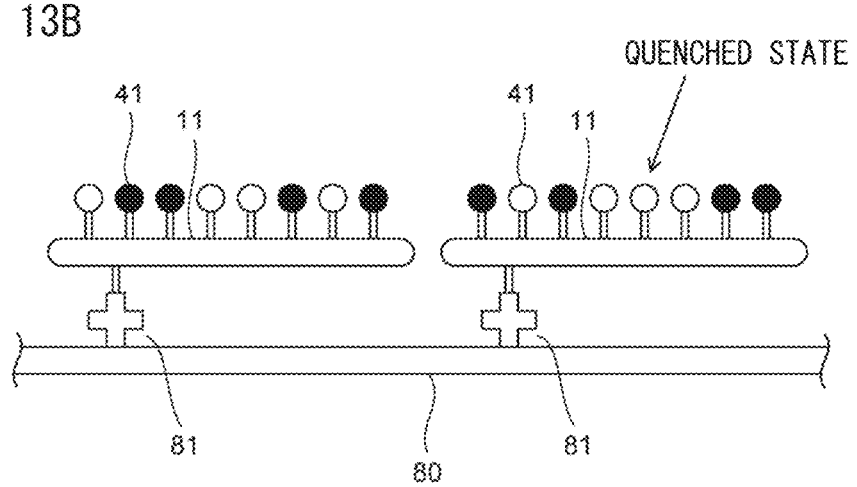
FIG. 13B is a schematic diagram showing that some of the fluorescent dyes are in the light emitting state in the information obtaining step according to Embodiments 1 to 4.
Figure 13C:
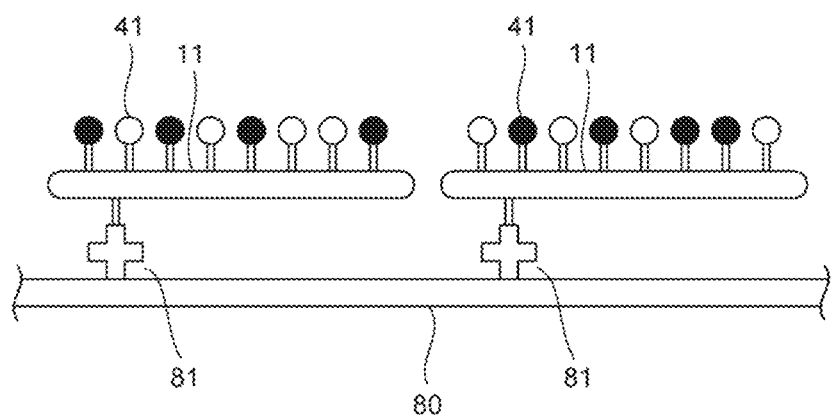
FIG. 13C is a schematic diagram showing that some of the fluorescent dyes are in the light emitting state in the information obtaining step according to Embodiments 1 to 4.

FIG. 12 is a flow chart showing the information obtaining step. In the description below, schematic diagrams shown in FIG. 13A to FIG. 13C are referenced as appropriate. FIG. 13A to FIG. 13C show the test substance 11 immobilized on the base plate 80.

Here, the fluorescent dye 41 is configured to be switched between a light emitting state in which the fluorescent dye 41 generates fluorescence and a quenched state in which the fluorescent dye 41 does not generate fluorescence, when excitation light is continually applied to the fluorescent dye 41. As the fluorescent dye 41, a commercially available dye can be used. In FIG. 13A to FIG. 13C, the fluorescent dye 41 in the light emitting state is indicated by a black circle, and the fluorescent dye 41 in the quenched state is indicated by a while circle.

As shown in FIG. 12, in step S101, the excitation light is applied to the fluorescent dyes 41 on the base plate 80. As shown in FIG. 13A, in the initial state, all of the fluorescent dyes 41 are in the light emitting state. When the excitation light starts to be applied in this state, fluorescence is excited from all of the fluorescent dyes 41. Then, when the excitation light is continually applied to the fluorescent dyes 41, the distribution of the fluorescent dyes 41 in the light emitting state changes as shown in, for example, FIG. 13B and FIG. 13C, with the lapse of time.

In step S102, while the excitation light is applied to the fluorescent dyes 41, image capturing of the generated fluorescence is performed, and images of the fluorescent dyes 41 are obtained. In step S102, the image capturing is repeated while the excitation light is being applied to the fluorescent dyes 41, and 3000 images are obtained, for example. Since the distribution of the fluorescent dyes 41 in the light emitting state changes in accordance with the lapse of time as described above, the distribution of fluorescence on the obtained images is different for the respective timings of the image capturing.

In step S103, whether a predetermined time period has elapsed and obtaining of necessary images has ended is determined. When obtaining of necessary images has been completed, the process is advanced to step S104. When the images are obtained in this manner, information regarding the structure of the test substance 11 can be obtained in a step of the latter stage.

The images may be obtained by steps based on the technique according to STORM, PALM, STED, or SIM, instead of steps S101 to S103. In a case where the images are obtained by the steps based on STORM, the fluorescent dye 41 is configured to be switched between an active state in which the fluorescent dye 41 generates fluorescence and an inactive state in which the fluorescent dye 41 does not generate fluorescence. Then, by the fluorescent dye 41 being switched between the active state and the inactive state by two kinds light, a plurality of images having different distribution of fluorescence are obtained, similarly to the above.

Subsequently, in step S104, a super-resolution image is created.

Figure 14:
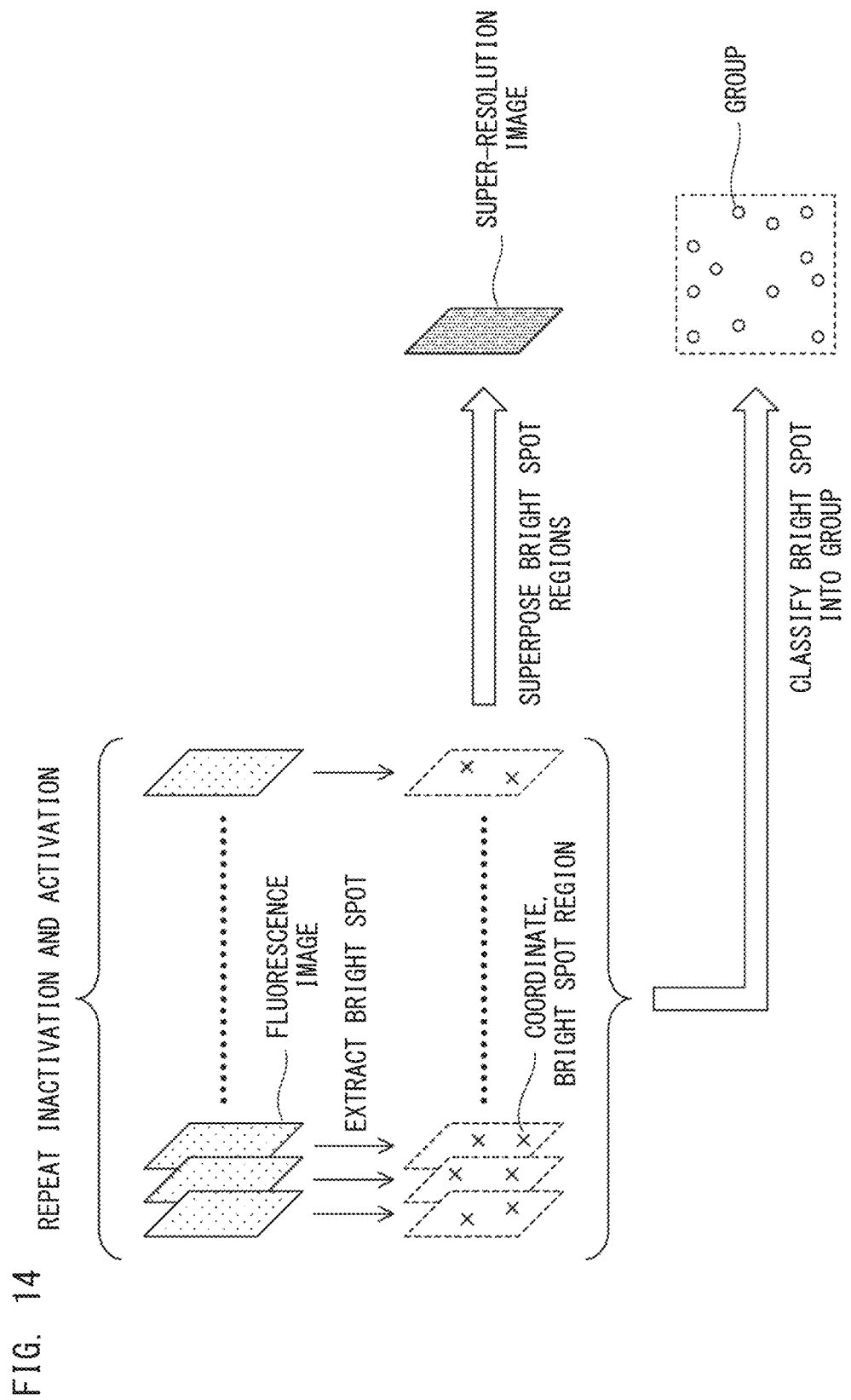
FIG. 14 is a diagram describing the procedure of obtaining a super-resolution image and classifying bright spots into a group in the information obtaining step according to Embodiments 1 to 4.

As shown in FIG. 14, a super-resolution image is created on the basis of a plurality of fluorescence images obtained in step S102 shown in FIG. 12. Specifically, for each fluorescence image, bright spots of fluorescence are extracted through Gauss fitting. Accordingly, on a two-dimensional plane, coordinates of each bright spot are obtained. Here, as a result of Gauss fitting, as to a bright spot of a fluorescence region that matches with a reference waveform in a predetermined range, a bright spot region of a size corresponding to this range is assigned. As to a bright spot of a fluorescence region that matches, at one point, with the reference waveform, a bright spot region of a lowest-level size is assigned. The bright spot regions obtained from each of the fluorescence images are superposed, whereby a super-resolution image is created.

Thus, in a case where 3000 fluorescence images are obtained in step S102, bright spots are extracted from the 3000 fluorescence images and the bright spot regions of the extracted bright spots are superposed, whereby a super-resolution image of the fluorescence images is created.

With reference back to FIG. 12, in step S105, information regarding the structure of the test substance 11 is obtained. In step S105, as information regarding the structure of the test substance 11, the size, the morphology, the structure, the aggregation degree, and the like regarding the test substance 11 are obtained.

In step S105, information regarding the structure of the test substance 11 is obtained in the following procedure.

As shown in FIG. 14, bright spots extracted at the creation of the super-resolution image obtained in step S104 shown in FIG. 12 are classified into a group corresponding to aggregated test substance 11. That is, all the bright spots extracted from the plurality of fluorescence images are mapped on a coordinate plane. Subsequently, the coordinate plane is scanned for a reference region of a predetermined size, and the number of bright spots contained in the reference region is obtained. Then, the position of a reference region in which the number of bright spots contained therein is greater than a threshold and greater than in the surrounding area is extracted, and the bright spots contained in the reference region at the extracted position are classified into one group. The one group thus obtained is regarded as one aggregate of the test substance 11.

The method for classifying bright spots into one group is not limited thereto, and another clustering technique may be employed. For example, a region that has a brightness not less than a predetermined threshold on a fluorescence image generated by totaling all fluorescence images may be regarded as one aggregate. Alternatively, a region that has a brightness not less than a predetermined threshold on a fluorescence image obtained by performing image capturing of fluorescence excited from all the fluorescent dyes 41 immediately after the start of step S101 in the information obtaining step may be regarded as one aggregate.

Subsequently, for each aggregate of the test substance 11, the following information is obtained on the basis of the super-resolution image. That is, as the size of the test substance 11, the length in the longitudinal direction, the length in the short direction, the perimeter, the area, and the like are obtained. As the morphology of the test substance 11, the aspect ratio, the circularity, the number of branches, the angle between branches, and the like are obtained. The aspect ratio is obtained by dividing the length in the longitudinal direction by the length in the short direction, for example. As the structure of the test substance 11, which among the primary structure, the secondary structure, the tertiary structure, and the quaternary structure of protein corresponds to the aggregate of the test substance 11 is obtained. As the aggregation degree of the test substance 11, the number of monomers forming the aggregate is obtained. The number of monomers is obtained by comparing the standard size of a monomer with the size of the aggregate.

In step S105, information regarding the structure of the test substance 11 is obtained on the basis of the super-resolution image. However, not limited thereto, information regarding the structure of the test substance 11 may be obtained on the basis of a fluorescence image obtained by performing image capturing of the fluorescence generated from the fluorescent dyes 41. For example, information regarding the structure of the test substance 11 may be obtained on the basis of a fluorescence image obtained by performing image capturing of the fluorescence generated from all the fluorescent dyes 41 immediately after the start in step S101. However, in this case, analysis cannot be performed at a resolution exceeding the diffraction limit of light. Therefore, it is preferable that information regarding the structure of the test substance 11 is obtained on the basis of a super-resolution image as described above.

With reference back to FIG. 12, in step S106, information obtained in step S105 is outputted. Specifically, the obtained information is displayed on a display unit implemented as a display. Other than this, the obtained information may be outputted as a sound from a speaker, or may be transmitted as digital data to another apparatus.

FIG. 15 is a schematic diagram showing a screen 90 displayed on the display unit in step S106.

The screen 90 includes images 91, 92 and a region 93. The image 91 is the super-resolution image obtained in step S104 shown in FIG. 12. The image 92 is an enlarged image of a portion of the image 91. The region 93 is a region in which to display the information regarding the structure of the test substance 11 obtained in step S105 shown in FIG. 12. When the screen 90 as shown in FIG. 15 is displayed in the information obtaining step, a doctor and the like, for example, can visually understand the super-resolution image and the information regarding the structure of the test substance 11, and thus, can smoothly diagnose the disease condition and determine an administration policy.

Verification of Embodiment 1

Next, the verification of Embodiment 1 performed by the inventors is described. In this verification, the inventors obtained super-resolution images in accordance with the procedure of Embodiment 1, and obtained super-resolution images in accordance with the procedure of Comparative Example in which impurities were not removed.

[Preparation of Specimen]

Amyloid β peptide 1-42 human (manufactured by Eisai) was diluted with CSF (manufactured by Access Biologicals), to prepare a plurality of specimens each containing a test substance and having different concentrations. The prepared specimens correspond to the specimen 10 of Embodiment 1.

[Preparation of Base Plate]

By the following method, glass base plates each modified with streptavidin were prepared. The prepared glass base plates correspond to the base plate 80 of Embodiment 1. (1) A through-hole having a 6 mm diameter was made in a silicone rubber sheet (TIGERS POLYMER CORPORATION, SR-50) and the silicone rubber sheet was attached to an MAS coated glass (manufactured by Matsunami Glass Ind., Ltd.). (2) 0.5 µL of 30 µg/mL biotin-bound BSA was dropped on the glass inside the silicone rubber sheet, and the resultant object was left to stand for one hour at room temperature. (3) By use of 20 µL of an HISCL washing liquid (manufactured by Sysmex Corporation), washing by pipetting was performed three times in total. (4) 20 µL of a 1% BSA/0.05% PBST solution was dropped and the resultant object was left to stand overnight at 4° C. (5) By use of 20 µL of the HISCL washing liquid, washing by pipetting was performed three times in total. (6) 20 µL of a 10 µg/mL streptavidin/1% BSA/0.05% PBST solution was dropped and the resultant object was left to stand for one hour at room temperature. (7) By use of 20 µL of the HISCL washing liquid, washing by pipetting was performed four times in total.

[Preparation of Other Substances]

Anti-human Amyloid β Mouse IgG (82E1) modified with biotin was prepared and was used as a first capture substance capable of binding to the base plate. The prepared first capture substance corresponds to the first capture substance 50 of Embodiment 1. Magnetic beads having an anti-DNP antibody bound thereto (Anti-DNP labeled antibody labeled beads (manufactured by Sysmex Corporation)) were used as a solid phase. The prepared solid phase corresponds to the solid phase 20 of Embodiment 1. Anti-human Amyloid β Mouse IgG (82E1) modified with DNP was prepared and was used as a second capture substance capable of binding to the solid phase. The prepared second capture substance corresponds to the second capture substance 30 of Embodiment 1. Anti-human Amyloid β Mouse IgG (82E1) modified with a silyl rhodamine-based fluorescent dye was prepared and was used as a fluorescence-labeled antibody. The prepared fluorescence-labeled antibody corresponds to the third capture substance 40 of Embodiment 1. A 5 mM DNP-Lys. solution was used as a releaser. The prepared releaser corresponds to the releaser used in Embodiment 1.

As the silyl rhodamine-based fluorescent dye, the one obtained through synthesis according to the description in the following document was used. The document referenced in synthesizing the fluorescent dye was Jonathan B Grimm et al., "A general method to improve fluorophores for live-cell and single-molecule microscopy", nature methods, VOL.12 NO.3 (2015) pp.244-250.

Procedure of Verification of Embodiment 1

(1) The first capture substance (Biotin-IgG), the second capture substance (DNP-IgG), and the fluorescence-labeled antibody (fluorescent dye-IgG) prepared as described above were mixed together, and the mixture was adjusted with an HISCL R3 diluent (manufactured by Sysmex Corporation) so as to have the composition as shown in the table below, whereby an antibody solution was prepared.

TABLE 1

| Composition of antibody solution | |
|---|---|
| Antibody | Antibody concentration (fmol/assay) |
| Biotin-IgG | 200 |
| DNP-IgG | 200 |
| Fluorescent dye-IgG | 200 |

(2) 80 µL of the antibody solution and 500 µL of the specimen were mixed together, and the mixture was allowed to react for 30 minutes at 37° C. (3) 20 µL of the solid phase was mixed thereto, and the resultant mixture was allowed to react for 15 minutes at 37° C. (4) The solid phase was collected by magnetic force, then the supernatant was removed (BF separation), and then, 20 µL of the HISCL washing liquid was added, and the resultant mixture was agitated. This step was performed three times in total. (5) After the BF separation, 10 µL of the 5 mM DNP-Lys. solution serving as the releaser was added, and the resultant mixture was agitated. This mixture was allowed to react for 10 minutes at 37° C. (6) After the BF separation, the supernatant was collected, and was dropped on the base plate. The resultant object was left to stand for two hours at room temperature. (7) By use of 20 µL of the HISCL washing liquid, washing by pipetting was performed three times in total. (8) The information obtaining step similar to that shown in FIG. 12 was performed by use of a super-resolution fluorescence microscope, and the test substance on the base plate was observed. Then, a super-resolution image was obtained.

PROCEDURE OF VERIFICATION OF COMPARATIVE EXAMPLE (1) The first capture substance (Biotin-IgG) prepared as described above was adjusted with the HISCL R3 diluent so as to attain 200 fmol/assay, and 80 µL of the resultant mixture was added to a base plate and was allowed to react for 30 minutes at 37° C. (2) After the supernatant was removed, washing was performed by use of 20 µL of the HISCL washing liquid. This step was performed three times in total. (3) 500 µL of the specimen was added, and the resultant mixture was allowed to react for 60 minutes at 37° C. (4) After the supernatant was removed, washing was performed by use of 20 µL of the HISCL washing liquid. This step was performed three times in total. (5) The fluorescence-labeled antibody (fluorescent dye-IgG) was adjusted with the HISCL R3 diluent so as to attain 200 fmol/assay, 80 µL of the resultant mixture was added to the base plate, and the resultant mixture was allowed to react for 60 minutes at 37° C. (6) After the supernatant was removed, washing was performed by use of 20 µL of the HISCL washing liquid. This step was performed three times in total. (7) The information obtaining step similar to that shown in FIG. 12 was performed by use of a super-resolution fluorescence microscope, and the test substance on the base plate was observed. Then, a super-resolution image was obtained.

With reference to FIGS. 16A to 16C, the verification result of Embodiment 1 is described.

FIG. 16A shows super-resolution images obtained through the procedure of verification of Embodiment 1. FIG. 16A shows super-resolution images obtained when arbitrary concentrations of the test substance in the specimen were employed. As shown in FIG. 16A, due to the resolution exceeding the diffraction limit, in each of the four super-resolution images, the shape of an aggregate of the test substance about 100 nm is displayed in a recognizable manner. Thus, according to Embodiment 1, a very small shape of the test substance exceeding the diffraction limit can be observed, and thus, it is considered that information regarding the structure of the test substance can be accurately obtained.

FIG. 16B shows fluorescence images each obtained by performing image capturing of fluorescence excited from all of the fluorescent dyes 41 immediately after the start of step S101 in the information obtaining step, in the procedure (8) of verification of Embodiment 1. The three fluorescence images shown in FIG. 16B are, from the left in order, the fluorescence images obtained when the concentrations of test substance in the specimen were 0 pM, 0.3 pM, and 1 pM, respectively. FIG. 16C is a graph showing the relationship between the number of bright spots on the three fluorescence images shown in FIG. 16B and the concentration of the test substance. As to the counting of the bright spots, each region having a brightness exceeding a predetermined threshold in a fluorescence image was defined as a bright spot region, and the number of specified bright spot regions was counted.

As shown in FIG. 16C, in Embodiment 1, when the concentration of the test substance is 0 pM, the number of bright spots is close to 0, and in accordance with increase in concentration, the number of bright spots increased. Thus, according to Embodiment 1, even when the concentration of the test substance is low, specific fluorescence detection regarding the test substance can be realized, while influence of impurities is suppressed.

With reference to FIGS. 17A to 17C, the verification result of Comparative Example is described.

FIG. 17A shows a super-resolution image obtained through the procedure of verification of Comparative Example. FIG. 17A is a super-resolution image obtained when the concentration of the test substance in the specimen was 0 pM. As shown in FIG. 17A, in Comparative Example, although the concentration of the test substance was 0 pM, a plurality of bright spots exist, and thus, it is seen that there is much noise light based on impurities. Therefore, in Comparative Example, since impurities are mixed with the test substance on the base plate, clear distinction between the test substance and the impurities are not realized, and thus, information regarding the structure of the test substance becomes difficult to be accurately obtained.

FIG. 17B shows fluorescence images each obtained by performing image capturing of fluorescence excited from all of the fluorescent dyes 41 immediately after the start of step S101 in the information obtaining step, in the procedure (7) of verification of Comparative Example. The three fluorescence images shown in FIG. 17B are, from the left in order, the fluorescence images obtained when the concentrations of the test substance in the prepared specimen were 0 pM, 0.3 pM, and 1 pM, respectively. FIG. 17C is a graph showing the relationship between the number of bright spots on the three fluorescence images shown in FIG. 17B and the concentration of the test substance. The counting of the bright spots was performed in a similar manner to that in the verification of Embodiment 1.

As shown in FIG. 17C, in Comparative Example, although the concentration of the test substance is 0 pM, several thousands of bright spots exist, and the number of bright spots has not increased in accordance with increase in concentration. Therefore, according to Comparative Example, due to influence of noise light based on impurities, specific fluorescence detection regarding the test substance is difficult.

Through the verifications above, it was found that, according to Embodiment 1, information regarding the structure of the test substance could be accurately obtained while influence of the impurities was suppressed by removing the impurities.

<Detection Apparatus>

Figure 18:
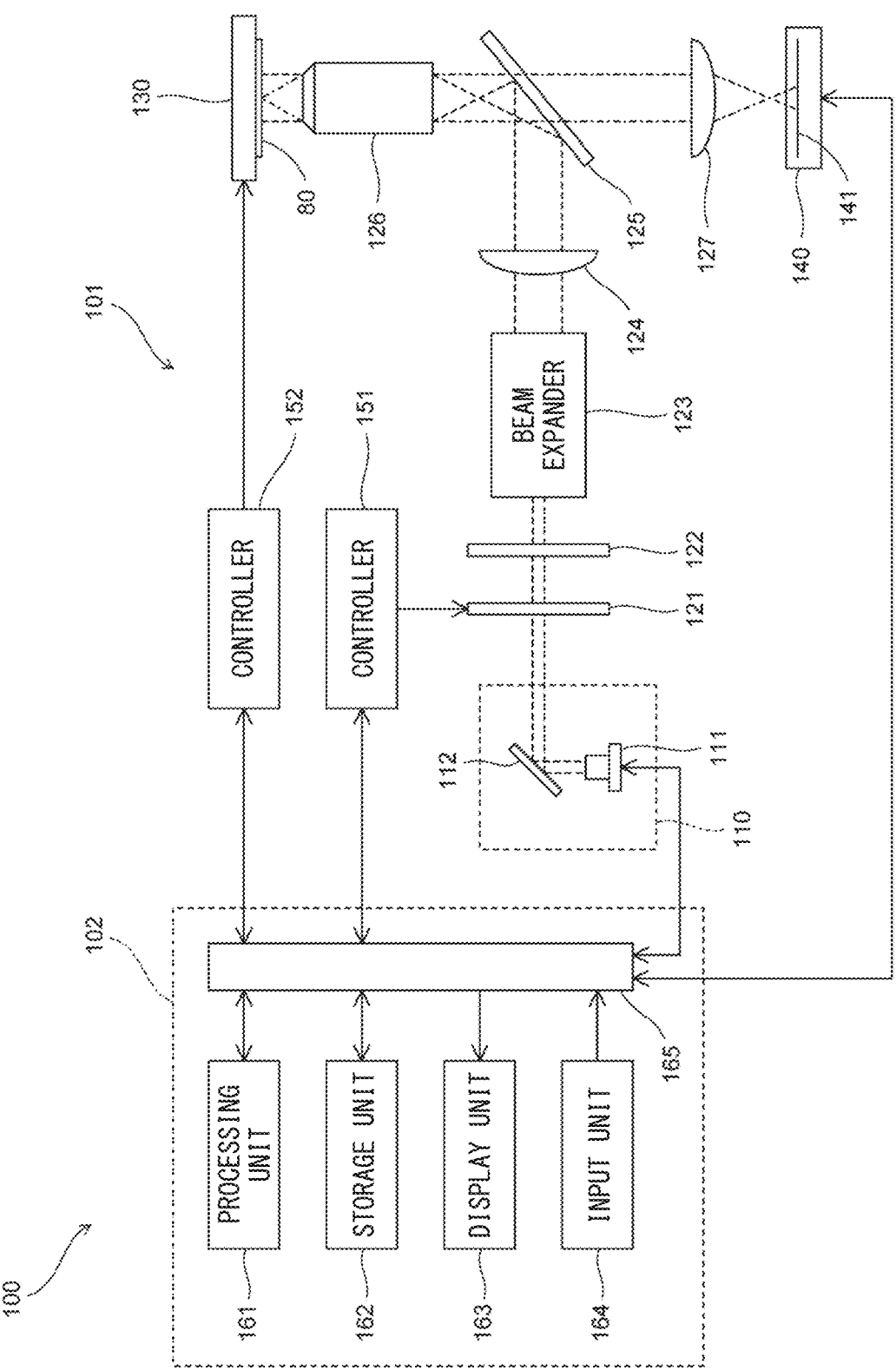
FIG. 18 is a schematic diagram showing a configuration of a detection apparatus for automatically performing the information obtaining step according to Embodiments 1 to 4.
Figure 19B:
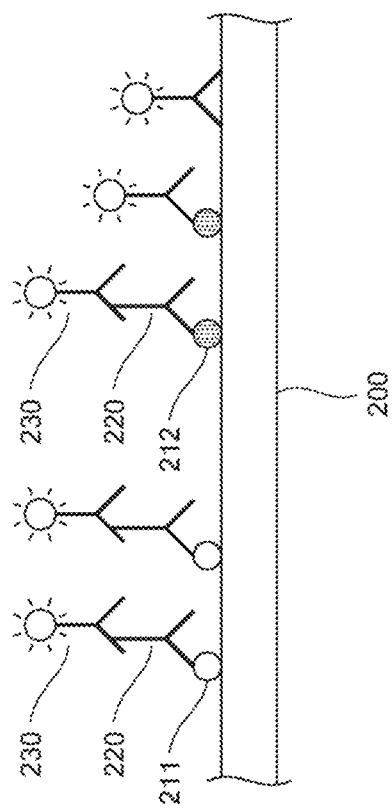
FIG. 19B is a schematic diagram for describing the configuration of the related art.
Figure 19A:
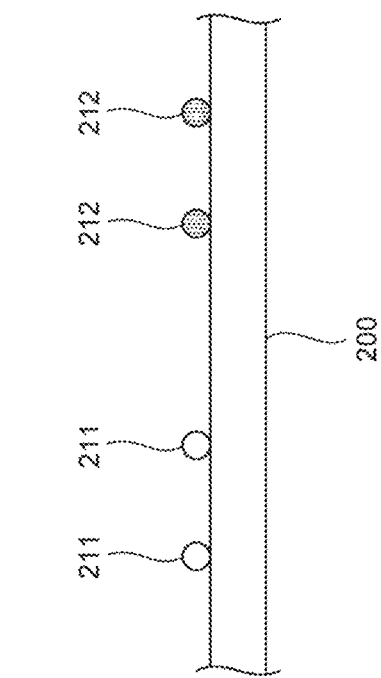
FIG. 19A is a schematic diagram for describing a configuration of related art.

As shown in FIG. 18, the detection apparatus 100 includes an information obtaining unit 101 and an information processing unit 102. The detection apparatus 100 is an apparatus for automatically performing each step in the information obtaining step shown in FIG. 12.

The information obtaining unit 101 includes a light source unit 110, a shutter 121, a ¼ wave plate 122, a beam expander 123, a condenser lens 124, a dichroic mirror 125, an objective lens 126, a condenser lens 127, a stage 130, an image capturing unit 140, and controllers 151, 152. On the stage 130, the base plate 80 having the test substance 11 immobilized thereon is set.

The light source unit 110 includes a light source 111 and a mirror 112. The light source 111 emits excitation light. As the light source 111, a laser light source is preferably used, but a mercury lamp, a xenon lamp, an LED, or the like may be used. The excitation light emitted from the light source 111 changes the state of the fluorescent dye 41 bound to the test substance 11 between the light emitting state and the quenched state, and causes the fluorescent dye 41 in the light emitting state to be excited to generate fluorescence. The mirror 112 reflects the excitation light from the light source 111 to guide the excitation light to the shutter 121.

In a case where the fluorescent dye 41 is configured to be switched between an active state in which the fluorescent dye 41 generates fluorescence and an inactive state in which the fluorescent dye 41 does not generate fluorescence, the light source unit 110 is configured to include two light sources, a mirror, and a dichroic mirror. In this case, one of the light sources emits light that causes the fluorescent dye 41 to enter the active state, and the other of the light source emits light that causes the fluorescent dye 41 to enter the inactive state. The optical axes of lights from the two light sources are caused to be aligned with each other by the mirror and the dichroic mirror.

The shutter 121 is driven by the controller 151, and performs switching between a state in which the excitation light emitted from the light source unit 110 is allowed to pass therethrough, and a state in which the excitation light emitted from the light source unit 110 is blocked. Accordingly, the time period of the application of the excitation light onto the test substance 11 is adjusted. The ¼ wave plate 122 converts the excitation light, which is linearly polarized light, emitted from the light source unit 110 into circularly polarized light. The fluorescent dye 41 reacts with excitation light in a predetermined polarization direction. Thus, by converting the excitation light emitted from the light source unit 110 into circularly polarized light, the polarization direction of the excitation light can be easily aligned with the polarization direction in which the fluorescent dye 41 reacts. Accordingly, the fluorescent dye 41 can be efficiently excited to generate fluorescence. The beam expander 123 widens the application region of the excitation light on the base plate 80. The condenser lens 124 collects the excitation light such that collimated light is applied from the objective lens 126 to the base plate 80.

The dichroic mirror 125 reflects the excitation light emitted from the light source unit 110, and allows fluorescence generated from the fluorescent dye 41 to pass therethrough. The objective lens 126 guides to the base plate 80 the excitation light reflected by the dichroic mirror 125. The stage 130 is driven by the controller 152 so as to be moved in the planar direction. Fluorescence generated from the fluorescent dye 41 on the base plate 80 passes through the objective lens 126 and the dichroic mirror 125. The condenser lens 127 collects fluorescence that has passed through the dichroic mirror 125 and guides the fluorescence to a light receiving surface 141 of the image capturing unit 140. The image capturing unit 140 captures an image of fluorescence applied on the light receiving surface 141, and generates a fluorescence image. The image capturing unit 140 is implemented by a CCD, for example.

The information processing unit 102 includes a processing unit 161, a storage unit 162, a display unit 163, an input unit 164, and an interface 165.

The processing unit 161 is a CPU, for example. The storage unit 162 is a ROM, a RAM, a hard disk, or the like. On the basis of programs stored in the storage unit 162 and through the interface 165, the processing unit 161 controls each unit in the information processing unit 102, the light source 111 of the light source unit 110, the image capturing unit 140, and the controllers 151, 152.

On the basis of programs stored in the storage unit 162, the processing unit 161 performs the information obtaining step shown in FIG. 12. That is, in the information obtaining step, the processing unit 161 drives the light source 111 and causes the image capturing unit 140 to receive fluorescence generated from the fluorescent dye 41, and drives the image capturing unit 140 to obtain fluorescence images. On the basis of the fluorescence images obtained by the image capturing unit 140, the processing unit 161 generates a super-resolution image. On the basis of the generated super-resolution image, the processing unit 161 obtains information regarding the structure of the test substance 11, and causes the display unit 163 to display a screen including the obtained information.

The display unit 163 is a display for displaying a process result and the like obtained by the processing unit 161. The display unit 163 displays the screen 90 shown in FIG. 15. The input unit 164 is a keyboard and a mouse for receiving inputs of instructions from an operator.

<Modification>

In the information obtaining step shown in FIG. 12, the test substance 11 on the base plate 80 is measured by means of a super-resolution fluorescence microscope having a resolution exceeding the diffraction limit of light. However, not limited thereto, the test substance 11 on the base plate 80 may be measured by means of a Raman microscope, a probe microscope, or an electron microscope. With a probe microscope and an electron microscope, the test substance 11 can be measured at a resolution exceeding the diffraction limit of light. In a case where measurement by use of fluorescence is not performed in the information obtaining step, for example, in a case where a Raman microscope or a probe microscope is used, the labeling step described above is omitted. When the labeling step is omitted, it becomes easy to cause the first capture substance 50 to bind to the binding site of the test substance 11, and thus, the test substance 11 can be more smoothly immobilized on the base plate 80.

The size, the morphology, and the aggregation degree regarding the test substance 11 in the information regarding the structure of the test substance 11 can be obtained if the test substance 11 is measured by use of a super-resolution fluorescence microscope, a Raman microscope, a probe microscope, or an electron microscope. The structure of the test substance 11 in the information regarding the structure of the test substance 11 can be obtained if the test substance 11 is measured by use of a super-resolution fluorescence microscope, a Raman microscope, or a probe microscope.

When the test substance 11 is measured by use of a Raman microscope, Raman spectra reflecting the molecules or the atoms which form the test substance 11, and an image reflecting the shape of the test substance 11 are obtained. Thus, according to a Raman microscope, as information regarding the structure of the test substance 11, the chemical bond can also be obtained in addition to the size, the morphology, the structure, and the aggregation degree. Specifically, as the chemical bond of the test substance 11, the kind, number, concentration, proportion, and the like regarding the molecules or the atoms which form the test substance 11 are obtained. In this case, in the region 93 of the screen 90 shown in FIG. 15, the obtained chemical bond of the test substance 11 is displayed, in addition to the size, the morphology, the structure, and the aggregation degree. For example, in the region 93, as the obtained chemical bond of the test substance 11, "C=O is at a concentration of . . . , C—H is at a concentration of . . . ", etc. is displayed.

What is claimed is:

1. A method for obtaining information of a test substance, the method comprising:
   forming a complex by causing a capture substance to bind to a test substance in a specimen;
   selectively collecting at least the complex from the specimen;
   immobilizing the complex collected from the specimen, onto a base plate; and
   obtaining information regarding a structure of the test substance from the complex immobilized on the base plate.

2. The method for obtaining the information of the test substance of claim 1, wherein
   in the obtaining of the information regarding the structure of the test substance, at least one of size, morphology, structure, and aggregation degree of the test substance is obtained.

3. The method for obtaining the information of the test substance of claim 1, wherein
   the capture substance includes a capture substance for labeling the test substance with fluorescence.

4. The method for obtaining the information of the test substance of claim 1, wherein
   the capture substance includes a capture substance capable of binding to a solid phase.

5. The method for obtaining the information of the test substance of claim 1, wherein
   the capture substance includes a capture substance capable of binding to the base plate.

6. The method for obtaining the information of the test substance of claim 3, wherein
   the capture substance for labeling the test substance with fluorescence includes an antibody labeled with a fluorescent dye; and
   in the forming of the complex, the antibody labeled with the fluorescent dye is caused to bind to the test substance.

7. The method for obtaining the information of the test substance of claim 4, wherein
   after the solid phase is caused to bind to the complex through the capture substance capable of binding to the solid phase, the solid phase is selectively separated in the collecting of the complex from the specimen.

8. The method for obtaining the information of the test substance of claim 7, wherein
in the collecting of the complex from the specimen, the complex is caused to be detached from the solid phase after the solid phase is selectively separated.

9. The method for obtaining the information of the test substance of claim 7, wherein
the solid phase includes a magnetic particle, and
the solid phase is selectively separated by attracting the magnetic particle by magnetic force.

10. The method for obtaining the information of the test substance of claim 7, wherein
the capture substance capable of binding to the solid phase includes an antibody which binds to the test substance and a second binding substance which binds to the solid phase,
the solid phase includes a second binding partner which specifically binds to the second binding substance, and
binding between the complex and the solid phase is realized by binding between the test substance and the antibody of the capture substance capable of binding to the solid phase and by specific binding between the second binding substance and the second binding partner.

11. The method for obtaining the information of the test substance of claim 1, wherein
the capture substance includes a capture substance capable of binding to the base plate and a capture substance capable of binding to a solid phase, and
the capture substance capable of binding to the base plate and the capture substance capable of binding to the solid phase are different from each other.

12. The method for obtaining the information of the test substance of claim 1, wherein
in the collecting of the complex from the specimen, the complex is separated from an impurity on the basis of at least one of a difference in specific gravity, a difference in size, a difference in electrical property, and a difference in immunoreaction between the complex and the impurity.

13. The method for obtaining the information of the test substance of claim 5, wherein
the capture substance capable of binding to the base plate includes an antibody which binds to the test substance and a binding substance which binds to the base plate,
the base plate includes a binding partner which specifically binds to the binding substance, and
after the antibody included in the capture substance capable of binding to the base plate is caused to bind to the test substance, the complex is immobilized on the base plate through specific binding between the binding partner and the binding substance, in the immobilizing of the complex onto the base plate.

14. The method for obtaining the information of the test substance of claim 1, wherein
after the collecting of the complex from the specimen, a capture substance capable of binding to the base plate is caused to bind to the test substance.

15. The method for obtaining the information of the test substance of claim 1, wherein
in the obtaining of the information regarding the structure of the test substance, an image of the test substance is obtained by performing image capturing of the test substance on the base plate.

16. The method for obtaining the information of the test substance of claim 1, wherein
in the collecting of the complex from the specimen, the test substance and an impurity are separated from each other, and
the test substance is a protein as a test target contained in the specimen and the impurity includes a protein other than the protein as the test target.

17. The method for obtaining the information of the test substance of claim 1, wherein
the test substance is amyloid β.

18. The method for obtaining the information of the test substance of claim 1, wherein
the obtaining of the information regarding the structure of the test substance is performed by means of a microscope having a resolution exceeding a diffraction limit of light.

19. A method for obtaining information of a test substance, the method comprising:
causing a magnetic particle to bind to a test substance in a specimen;
selectively collecting at least the test substance from the specimen by use of the magnetic particle bound to the test substance;
immobilizing the test substance collected from the specimen, onto a base plate; and
obtaining information regarding a structure of the test substance from the test substance immobilized on the base plate.

20. A method for obtaining information of a test substance, the method comprising:
forming a complex by causing a capture substance including a fluorescent dye to bind to a test substance in a specimen;
selectively collecting at least the complex from the specimen;
immobilizing the complex collected from the specimen, onto a base plate; and
obtaining information regarding a structure of the test substance on the basis of bright spots corresponding to fluorescence emitted from a plurality of fluorescent dyes each bound to the complex immobilized on the base plate.

* * * * *